(12) United States Patent
Danthi et al.

(10) Patent No.: US 7,300,940 B2
(45) Date of Patent: Nov. 27, 2007

(54) INTEGRIN α-V β-3 ANTAGONISTS FOR USE IN IMAGING AND THERAPY

(75) Inventors: S. Narasimhan Danthi, Germantown, MD (US); King C. Li, Bethesda, MD (US); Christopher A. Burnett, College Park, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 492 days.

(21) Appl. No.: 10/911,988

(22) Filed: Aug. 4, 2004

(65) Prior Publication Data

US 2006/0030575 A1    Feb. 9, 2006

(51) Int. Cl.
*C07D 239/42* (2006.01)
*A61K 31/505* (2006.01)

(52) U.S. Cl. ...................................... 514/275; 544/332
(58) Field of Classification Search ................. 544/332; 514/275

See application file for complete search history.

(56) References Cited

U.S. PATENT DOCUMENTS

| 5,741,796 A | 4/1998 | Hartman et al. |
| 2002/0071843 A1 | 6/2002 | Li et al. |
| 2003/0186987 A1 | 10/2003 | Kees et al. |

FOREIGN PATENT DOCUMENTS

WO    WO 99/52879 A1    10/1999

OTHER PUBLICATIONS

Agrez et al., The alpha-v-beta-6 Integrin induces gelatinase B secretion in colon cancer cells, Int. J. Cancer, 81, pp. 90-97, 1999.*
Brooks et al., Integrin alpha-v-beta-3: A therapeutic target, DN&P, 10(8), pp. 456-461, Oct. 1997.*
Gladson et al., Vitronectin Expression in Differentiating Neuroblastic Tumors, American Journal of Pathology, vol. 150, No. 5, pp. 1631-1646, May 1997.*
Kim et al., Vitronectin-driven Human Keratinocyte Locomotion Is Mediated by the alpha-v-beta-5 Integrin Receptor, The Journal of Biological Chemistry, vol. 269, No. 43, pp. 26928-26932, Oct. 1994.*
Nip et al., The role of the Integrin vitronectin receptor, alpha-v-beta-3 in melanoma metastasis, Cancer and Metastasis Reviews, 14, pp. 241-252, 1995.*
Raynal et al., Bone Sialoprotein Stimulates in vitro Bone Resorption, Endocrinology, vol. 137, No. 6, pp. 2347-2354, 1996.*
Schvartz et al., Vitronectin, The International Journal of Biochemistry & Cell Biology, 31, pp. 539-544, 1999.*
Simone, Oncology: Introduction, Cecil Textbook of Medicine, 20th Edition, vol. 1, pp. 1004-1010, 1996.*
Blaszykowski, Christophe et al.; "N-Silyl-Tethered Radical Cyclizations: A New Synthesis of γ-Amino Alcohols"; 2003, *Organic Letters*, vol. 5, No. 8, pp. 1341-1344.
Duggan, Mark E. et al.; "Nonpeptide $\alpha_v\beta_3$ Antagonists. 1. Transformation of a Potent, Integrin-Selective $\alpha_{IIb}\beta_3$ Antagonist into a Potent $\alpha_v\beta_3$ Antagonist"; 2000, *J. Med. Chem.*, vol. 43, pp. 3736-3745.
Ensch, Corinne et al.; "Enantioselective Entry to the *Homalium* Alkaloid Hoprominol; Synthesis of an (R,R,R)-Hoprominol Derivative"; 2003, *Helvetica Chimica Acta*. vol. 86, pp. 233-246.
Gray, C.J. et al.; "The Synthesis of An α-Azaornithine Derivative and its Reaction with Trypsin"; 1975, *Tetrahedran*, vol. 31, pp. 2940-2943.
Hood, John D. et al.; "Tumor Regression by Targeted Gene Delivery to the Neovasculature"; 2002, Science, vol. 296, pp. 2404-2407.
Mattingly, Phillip G.; "Mono-Protected Diamines. $N^2$-tert-Butoxycarbonyl α,co-Alkanediamine Hydrochiorides from Amino alcohols"; 1990, *Synthesis Papers*, pp. 366-368.
Burnett, Christopher A. et al.; "Synthesis, in vitro, and in vivo characterization of an integrin $\alpha_v\beta_3$-targeted molecular probe for optical imaging of tumor"; 2005, *Bioorganic & Medicinal Chemistry*, vol. 13, pp. 3763-3771.

* cited by examiner

*Primary Examiner*—Deepak Rao
(74) *Attorney, Agent, or Firm*—Townsend and Townsend and Crew LLP; M. Henry Heines

(57) ABSTRACT

Integrin receptor antagonists whose molecular structure includes a tetrahydropyridimidinylaminoethyloxybenzoyl group on a sulfonylamino-β-alanine nucleus exhibit increased binding affinity for the αvβ3 receptor when further substituted on the sulfonyl moiety with an N-amino alkycarbamyl group or a butyloxycarbonylamino alkylcarbamoyl group or similar groups.

48 Claims, 9 Drawing Sheets

INTEGRIN α-V β-3 ANTAGONISTS FOR USE IN IMAGING AND THERAPY

BACKGROUND OF THE INVENTION

1. Field of the Invention

This invention resides in the field of cell surface molecules of mammalian cells, and particularly to ligands that bind to such molecules for purposes of inhibiting the biological activity of the cells, adhering a detectable label or imaging moiety to the cells, and of delivering therapeutic agents to the cells.

2. Description of the Prior Art

Receptors on the surfaces of mammalian cells take part in many biological processes that the cells perform, including cell invasion and cell proliferation. One particular receptor that has implications for a wide variety of disease conditions is the vitronectin receptor αvβ3 (which is also reported as αvβ3). This receptor is a member of the integrin superfamily of receptors and is associated with various cells including cells of the angiogenic endothelium and osteoclasts. As reported by Hood, J. D., et al., "Tumor Regression by Targeted Gene Delivery to the Neovasculature," *Science* 296: 2404-2407 (28 Jun. 2002), αvβ3 plays a key role in endothelial cell survival during angiogenesis in vivo and potentiates the internalization of such viruses as foot-and-mouth disease virus, rotavirus, and adenovirus. By virtue of this potentiation, this receptor can be used to effect gene delivery by viral methods as well as other methods. Further useful qualities of the receptor are discussed by Duggan, M. E., et al., "Nonpeptide αvβ3 antagonists. 1. Transformation of a Potent, Integrin-Selective $a_{IIb}\beta_3$ Antagonist into a Potent $a_v\beta_3$ Antagonist," *J. Med. Chem.* 43(20): 3736-3745 (2000), who report that αvβ3 is highly expressed in osteoclasts but not present in osteoblasts. This has led the authors to investigate use of the nonpeptide antagonists as pharmaceutical agents for the treatment of osteoporosis. Further discussion by the same authors is found in Hartmann, G. D., et al., U.S. Pat. No. 5,741,796, issued Apr. 21, 1998, which cites the administration of the same nonpeptide antagonists in the treatment of hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment. Other nonpeptide antagonists of vβ3 are reported in International Patent Application Publication No. WO 99/52879 (applicant: American Home Products Corporation, inventors: Kees, K. L., et al., international publication date: 21 Oct. 1999) and its United States counterpart, United States Pre-Grant Publication No. U.S. 2003 0186967 A1, Kees, K. L., et al., publication date 02 Oct. 2003. These Kees et al. publications report the activity of vβ3 in mediating the invasion of malignant melanoma cells into healthy tissue, in protecting cells against apoptosis, in mediating the growth of solid tumors, and in liver metastasis. Peptide antagonists have also been studied, notably antibodies to avβ3, as well as proteins that possess the three-amino acid sequence arginine-glycine-aspartic acid (RGD). Such proteins include echistatin, vitronectin, osteopontin, and bone sialoprotein. Non-peptide mimics of these proteins have also been studied.

SUMMARY OF THE INVENTION

A new class of integrin receptor antagonists with unusually high binding affinity for avβ3 has now been discovered. This class is defined by the following formula:

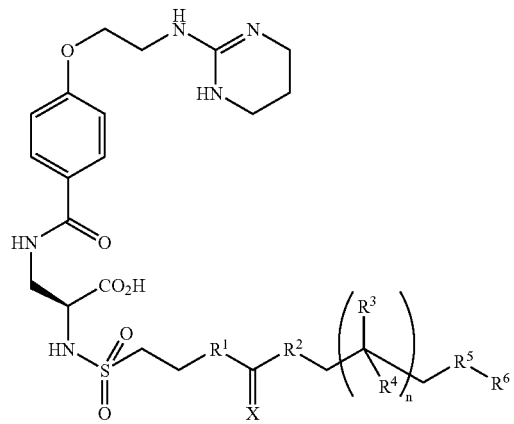

in which:

X is either NH, O, or S;

n is zero or a positive integer;

$R^1$ is either $CH_2$, NH, O, or S;

$R^2$ is either $CHR^7$, $NR^7$, O or S, in which $R^7$ is H or alkyl;

$R^3$ and $R^4$, which are either the same or different from each other, are either H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, or (hydroxy-substituted aryl) alkyl;

$R^5$ is either $CH_2$, NH, O, or S; and $R^6$ is either H or $C(=Y)-R^8-R^9$, in which:

Y is either NH, O, or S;

$R^8$ is either $CHR^{10}$, $NR^{10}$, O, or S, in which $R^{10}$ is H or alkyl; and $R^9$ is either H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, or (hydroxy-substituted aryl)alkyl.

This invention resides in the compounds themselves and in pharmaceutical compositions containing one or more of the compounds together with a pharmaceutically acceptable carrier. The invention also resides in the administration of the compounds or pharmaceutical compositions containing the compounds to mammals afflicted with a condition that is mediated by an integrin receptor, and most notably αvβ3, as treatment for the condition. The invention further resides in the administration of the imaging agents that contain the compounds linked to a detectable moiety, or pharmaceutical compositions of such imaging agents, as part of the imaging of integrin receptor cells, again most notably αvβ3-bearing cells, in the mammal. As will be noted from the description that follows, this invention further resides in the treatment and prevention of various disease conditions that are associated with the biological activity of integrin receptors, most notably αvβ3, by either blocking, i.e., inhibiting, the receptor, or by modifying cells that bear these receptors on their surfaces by delivering genes or other therapeutic agents to the cells through the receptor.

Further embodiments, applications, and aspects of the invention will become apparent from the description that follows.

DETAILED DESCRIPTION OF THE INVENTION AND PREFERRED EMBODIMENTS

Figure 1A:
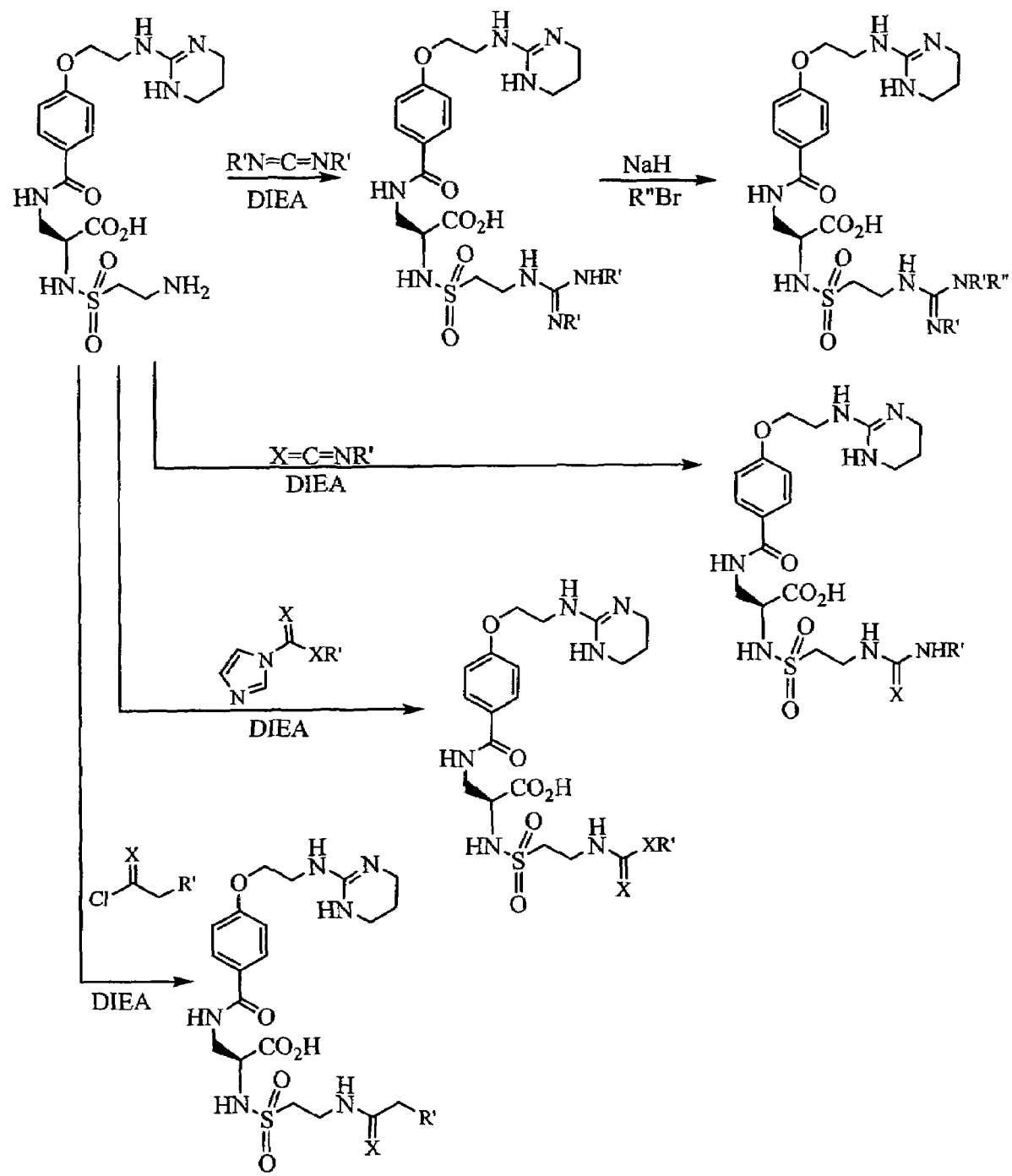
FIG. 1a illustrates four synthetic routes to compounds within the scope of the invention.

The term "alkyl" as used in this specification and the appended claims includes straight-chain and branched-chain groups as well as saturated and unsaturated groups. Saturated groups are preferred, and straight-chain groups are likewise preferred. Preferred alkyl chain lengths are 1 to 6 carbon atoms, and preferably 1 to 3. The term "cycloalkyl" includes monocyclic as well as multicyclic structures, including fused cyclic structures, and includes both saturated and unsaturated structures. Preferred cycloalkyls are saturated monocyclic structures, most preferably those of 5 to 7 carbon atoms. The term "aryl" includes both single-ring and fused-ring groups. The phrase "independently selected from" is used in certain claims following the recitation of two or more symbols appearing in the generic formula and is followed by lists of radicals that the symbols represent. The phrase is intended to indicate that the two or more symbols can be the same or different, i.e., the selection of a radical from the list for one such symbol is independent of the selection of a radical from the same list for another such symbol.

Within the scope of the generic formula, certain subgenera are preferred. The groups designated $R^3$, $R^4$, and $R^9$, which are either all different or any two or all of which the same, are preferably H, $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, or (hydroxy-substituted phenyl)-substituted $C_1$-$C_6$ alkyl. In more preferred embodiments, $R^3$ and $R^4$, which again are either the same or different, are H or $C_1$-$C_3$ alkyl. Particularly preferred groups for $R^9$ are H or $C_1$-$C_6$ alkyl. Preferred groups for $R^6$ are H and C(=O)—O—$R^9$, in which $R^9$ is $C_1$-$C_6$ alkyl.

The antagonists of the present invention can be administered either in the form indicated by the above formula or as salts resulting from combinations of the antagonists with pharmaceutically acceptable acids or bases. Examples of such acids are hydrochloric acid, sulfuric acid, nitric acid, phosphoric acid, and organic acids such as acetic acid, oxalic acid, succinic acid, and maleic acid. Examples of cations from which salts can be formed are alkali metals and alkaline earth metals, specific examples of which are sodium, potassium, calcium and magnesium. The antagonists can also be administered as esters, carbamates, amides, or other pro-drug forms that will convert to the active antagonists in vivo.

In certain applications and methods in accordance with this invention, notably those in which the antagonists function as inhibitory agents to block the activity of the αvβ3 receptor, the antagonists will serve their purpose alone, while in others they will be combined with therapeutic agents, genes, vehicles such as liposomes, micelles, or nanoparticles, or detectable labels. In most cases, however, the antagonists will be administered in combination with one or more pharmaceutically acceptable carriers, such as solvents, diluents, surfactants, dispersing agents, and other adjuvants known for their effectiveness as additives to pharmaceutical formulations. Examples of solid carriers are starch, lactose, dicalcium phosphate, microcrystalline cellulose, sucrose and kaolin. Examples of liquid carriers are sterile water, polyethylene glycols, non-ionic surfactants, and edible oils such as corn oil, peanut oil, and sesame oils. Other types of adjuvants include flavoring agents, coloring agents, preservatives, and antioxidants such as vitamin E, ascorbic acid, butylated hydroxytoluene, and butylated hydroxyanisole. Administration can be achieved orally or parentally, such as by intravenous, intramuscular, or subcutaneous methods. Formulations for oral administration, such as tablets, capsules, dispersible powders, granules, solutions or suspensions, may contain from about 0.05% to about 5% of a suspending agent, syrups containing from about 10% to about 50% sugar, or elixirs containing from about 20% to about 50% ethanol. Formulations for parenteral administration may contain from about 0.05% to about 5% of a suspending agent in an isotonic medium. In general, the active ingredient itself in most cases will comprise from about 5% to about 90% by weight of the formulation, and preferably from about 25% to about 60% by weight.

When the antagonists of the present invention are administered for purposes of delivering a therapeutic agent or for attaching a detectable moiety to (i.e., labeling) the αvβ3 receptor-bearing cells, the therapeutic agent or the detectable moiety is combined with the antagonist through a pharmaceutically acceptable linker. Such linkers include those that join one detectable moiety to a single antagonist of the above formula, and those that join two or more detectable moieties to a single antagonist, as well as those that join one detectable moiety to two or more antagonists. In certain cases, the joining of two or more detectable moieties to one antagonist produces a greater signal from the cell or may allow imaging to be performed in more than one imaging modality.

The linker can provide either a covalent or a non-covalent linkage, preferably through functional groups on the detectable moiety, the antagonist, or both. The linkage can be made at any point on the antagonist formula as shown above, but is preferably at a site in the region extending from the $R^1$ moiety to the $R^6$ moiety in the formula. Most preferably, the linkage is at the $R^6$ moiety or at an atom within the $R^6$ moiety. Examples of chemically reactive functional groups on both the antagonist and the detectable moiety that can be employed for this purpose are amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups. The linkage chemistry is well known among those skilled in the art.

One type of reactive moiety capable of reaction with sulfhydryl, imidazolyl, thioether, phenol, and amino groups are α-haloacetyl compounds of the type X—CH$_2$CO— where X is either Br, Cl or I. N-Maleimide derivatives are also selective towards sulfhydryl groups, and under certain conditions, to amino groups as well. Carbonyl groups such as aldehyde functions may be reacted with weak protein bases at a pH that will cause protonation of nucleophilic protein side-chain functions. Weak bases include 1,2-aminothiols such as those found in N-terminal cysteine residues, which selectively form stable 5-membered thiazolidine rings with aldehyde groups. Other suitable weak bases are phenyl hydrazones. Aldehydes and ketones may also be reacted with amines to form Schiff's bases, which can be stabilized through reductive amination. Alkoxyamino moieties readily react with ketones and aldehydes to produce stable alkoxamines.

Examples of reactive moieties capable of reaction with carboxyl groups are diazo compounds such as diazoacetate esters and diazoacetamides. Carboxylic acid modifying reagents such as carbodiimides, which react through O-acylurea formation followed by amide bond formation, can also be employed, and linking can be facilitated through insertion of an amine or through direct antagonist-detectable moiety coupling. Examples of useful water soluble carbodiimides are 1-cyclohexyl-3-(2-morpholinyl-4-ethyl)carbodiimide (CMC) and 1-ethyl-3-(3-dimethylaminopropyl)carbodiimide (EDC). Other useful carboxylic acid modifying reagents include isoxazolium derivatives such as Woodward's Reagent K, chloroformates such as p-nitrophenylchloroformate, carbonyldiimidazoles such as 1,1'-carbonyldiimidazole, and N-carbalkoxydihydroquinolines such as N-(ethoxycarbonyl)-2-ethoxy-1,2-dihydroquinoline.

Functional groups in the detectable moiety and/or antagonist can also be converted to other functional groups prior to reaction to confer additional reactivity or selectivity. Amines can thus be converted to carboxylic acids with reagents such as dicarboxylic anhydrides, or to thiols with reagents such as N-acetylhomocysteine thiolactone, S-acetylmercaptosuccinic anhydride, 2-iminothiolane or thiol-containing succinimidyl derivatives. Thiols can be converted to carboxylic acids with reagents such as α-haloacetates, or to amines with reagents such as ethylenimine or 2-bromoethylamine. Carboxylic acids can be converted to amines with reagents such as carbodiimides followed by diamines. Alcohols can be converted to thiols with reagents such as tosyl chloride followed by transesterification with thioacetate and hydrolysis to the thiol with sodium acetate.

Non-covalent linkages can be achieved by electrostatic charge interactions, such as between a polylysilyl-functionalized detectable moiety and a polyglutamyl-functionalized antagonist, through chelation in the form of stable metal complexes or through a high affinity binding interaction such as avidin/biotin binding. Further non-covalent linkages are those involving avidin or streptavidin and biotin. When both the antagonist and the detectable moiety are biotinylated, they can be conjugated to each other by avidin. Non-covalent coupling can be achieved by way of bispecific immunoglobulin linkers. Examples are bispecific IgG and chemically engineered bispecific F(ab)'$_2$ fragments.

The linker can also include a spacer separating two reactive moieties. Spacers permit bifunctional linkers to react with specific functional groups on the molecules and minimize any interference in the binding affinity of the antagonist for the receptor as well as in the functionality of the detectable moiety. The nature of the spacer can also have a bearing on the targeting ability and general stability of the ultimate product. Labile linkages can be formed for example by incorporating spacer arms that are biodegradable or chemically sensitive or that incorporate enzymatic cleavage sites. Spacers that are polymeric in nature can act as surfactants and can enhance the stability of the conjugate. The spacer can also contain reactive moieties through which surface crosslinking can occur.

In embodiments of the invention in which the antagonist is joined to a detectable moiety for imaging or detection in general, any moiety capable of detection either directly or indirectly in an imaging procedure known to those skilled in the art can be used. Moieties can be used that emit or can be caused to emit detectable radiation, such as by radioactive decay, fluorescence excitation, or spin resonance excitation. Moieties that affect local electromagnetic fields, such as paramagnetic, superparamagnetic, ferrimagnetic or ferromagnetic species, can likewise be used. Still further moieties are those that absorb or scatter radiation energy, such as chromophores, particles (including gas- or liquid-containing vesicles), heavy elements and compounds of heavy metals. Moieties that generate a detectable substance, such as gas microbubble generators, can also be used.

For magnetic resonance imaging, examples of specific detectable moieties are chelated paramagnetic metal ions such as Gd, Dy, Fe, and Mn, especially when chelated by macrocyclic chelant groups including tetraazacyclododecane chelants such as DOTA, D03A, HP-DO3A, and analogues thereof, or by linker chelant groups such as DTPA, DTPA-BMA, EDTA, and DPDP. Other examples are metal radionuclides such as $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb and $^{141}$Ce. Still further examples are superparamagnetic iron oxide crystals.

Other examples of detectable moieties are chelatable metal or polyatomic metal-containing ions (such as TcO), where the metal has an atomic number greater than 37, paramagnetic species such as a transition metal or lanthanide, or radioactive isotopes, polyatomic clusters or crystals containing high atomic number atoms that display cooperative magnetic behavior such as superparamagnetism, ferrimagnetism or ferromagnetism or that contain radionuclides, chromophores (including fluorescent and phosphorescent species), structures or groups having electrical impedance varying characteristics, such as by virtue of an extensive delocalized electron system.

Examples of chelating agents are polyphosphates such as sodium tripolyphosphate and hexametaphosphoric acid, aminocarboxylic acids such as ethylenediaminetetraacetic acid, N-(2-hydroxy)ethylene-diaminetriacetic acid, nitrilotriacetic acid, N,N-di(2-hydroxyethyl)glycine, ethylenebis (hydroxyphenylglycine) and diethylenetriamine pentacetic acid, 1,3-diketones such as acetylacetone, trifluoroacetylacetone, and thenoyltrifluoroacetone, hydroxycarboxylic acids such as tartaric acid, citric acid, gluconic acid, and 5-sulfosalicyclic acid, polyamines such as ethylenediamine, diethylenetriamine, triethylenetetraamine, and triaminotriethylamine, aminoalcohols such as triethanolamine and N-(2-hydroxyethyl)ethylenediamine, aromatic heterocyclic bases such as 2,2'-diimidazole, picoline amine, dipicoline amine and 1,10-phenanthroline, phenols such as salicylaldehyde, disulfopyrocatechol, and chromotropic acid, aminophenols such as 8-hydroxyquinoline and oximesulfonic acid, oximes such as dimethylglyoxime and salicylaldoxime; peptides containing a proximal chelating functionality such as polycysteine, polyhistidine, polyaspartic acid, or polyglutamic acid, Schiff bases such as disalicylaldehyde 1,2-propylenediimine, tetrapyrroles such as tetraphenylporphin and phthalocyanine, sulfur compounds such as toluenedithiol, meso-2',3-dimercaptosuccinic acid, dimercaptopropanol, thioglycolic acid, potassium ethyl xanthate, sodium diethyldithiocarbamate, dithizone, diethyl dithiophosphoric acid, and thiourea, synthetic macrocyclic compounds such as dibenzo[18]crown-6, $(CH_3)_6$-[14]-4,11]-diene-$N_4$, and (2.2.2-cryptate), and phosphonic acids such as nitrilotrimethylene-phosphonic acid, ethylenediaminetetra (methylenephosphonic acid), and hydroxyethylidenediphosphonic acid. Many chelating agents include a polycarboxylic acid group. Examples are ethylenediamine-N,N,N',N'-tetraacetic acid (EDTA), N,N,N',N'',N''-diethylene-triamine-pentaacetic acid (DTPA), 1,4,7,10-tetraazacyclododecane-N,N',N'',N'''-tetraacetic acid (DOTA), 1,4,7,10-tetraazacyclo-dodecane-N,N',N''-triacetic acid (DO3A), 1-oxa-4,7,10-triazacyclododecane-N,N',N''-triacetic acid (OTTA), and trans(1,2)-cyclohexanodiethylene-triamine-pentaacetic acid (CDTPA).

Examples of non-metal atomic moieties that can serve as detectable moieties are radioisotopes such as $^{123}I$ and $^{131}I$ as well as non-zero nuclear spin atoms such as $^{18}F$ and heavy atoms such as I. Such detectable moieties, and preferably a plurality thereof, such as 2 to 200, can be covalently bonded to a linker backbone, either directly using conventional chemical synthesis techniques or via a supporting group such as a triiodophenyl group.

Detectable moieties that are organic chromophores and fluorophores include groups having an extensive delocalized electron system, such as cyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis (dithiolene) complexes, bis(benzene-dithiolate) complexes, iodoaniline dyes, bis(S,O-dithiolene) complexes. Specific examples of chromophores are xylene cyanole, fluorescein, dansyl, NBD, indocyanine green, DODCI, DTDCI, DOTCI and DDTCI. Further examples are fluorescein derivatives, rhodamine derivatives, coumarins, azo dyes, metallizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryryl dyes, diaryl carbonium dyes, triaryl carbonium dyes, phthalocyanine dyes, quinophthalone dyes, triphenodioxazine dyes, formazan dyes, phenothiazine dyes such as methylene blue, azure A, azure B, and azure C, oxazine dyes, thiazine dyes, naphtholactam dyes, diazahemicyanine dyes, azopyridone dyes, azobenzene dyes, mordant dyes, acid dyes, basic dyes, metallized and premetallized dyes, and xanthene dyes.

Particulate species can also serve as detectable moieties. Some of these species contain a matrix or shell that carries or contains the detectable moiety. In others, the particle matrix is itself the detectable moiety. Examples of the first group are nanoparticles, micelles, liposomes, microballoons and microbubbles, containing a liquid, gas or solid phase which contains the detectable moiety such as an echogenic gas or a precursor thereof, a chelated paramagnetic metal or radionuclide, or a water-soluble iodinated X-ray contrast agent; porous particles loaded with a paramagnetic metal or other detectable moiety, and solid particles such as inert biotolerable polymers, onto which the detectable moiety, such as a dye, is bound or coated. Examples of particles that serve alone as detectable moieties are light scattering organic or inorganic particles, magnetic particles, nanoparticles, and dye particles.

The means by which a particle is attached to the antagonist will depend on the nature of the particle surface. For inorganic particles, the linkage can be an interaction with a metal binding group (e.g. a phosphate, phosphonate or oligo or polyphosphate group) on the antagonist or on a linker attached to the antagonist. For organic particles, antagonist attachment can be achieved through covalent bonding between groups on the particle surface and reactive groups in the antagonist to form amide or ester linkages, for example, or by covalent attachment of antagonist and particle to a linker.

For non-solid particles such as droplets and vesicles, the linker may contain hydrophobic anchor groups, for example saturated or unsaturated $C_{12-30}$ chains, which will penetrate the particle surface and bind antagonist to particle. Thus for phospholipid vesicles, the linker may serve to bind the antagonist covalently to a phospholipid compatible with the vesicle membrane.

Conditions that are mediated by integrin receptors and that can be inhibited or treated by administration of one or more compounds within the scope of the invention include, but are not limited to:
  cancer (notably tumor metastasis and tumor growth)
  angiogenesis (as in cancer, diabetio retinopathy, and rheumatoid arthritis)
  restenosis following balloon angioplasty or stent implantation
  inflammation such as that associated with rheumatoid arthritis or psoriasis,
  bone diseases such as Paget's disease, osteopenia induced by bone metastases, immobilization and glucocorticoid treatment, periodontal disease, hyperparathyroidism and rheumatoid arthritis, and viral infections.

The antagonists of the present invention are readily prepared by conventional methods. Depending on whether the $R^6$ group is H or C(=Y)—$R^8$—$R^9$, an amino alcohol or an N-alkoxy carbonyl or other appropriately substituted alcohol can serve as the starting material. Using an N-Boc amino alcohol as an example, this starting material can be reacted with a carbonyldiimidazole to obtain an O-carbonylimidazole derivative of the alcohol, which can then coupled to the 4-[2-(3,4,5,6-tetrahydropyrimidin-2-ylamino)ethyloxy]benzoyl-2-(S)-aminoethylsulfonylamino-β-alanine, which is the antagonist described by Hood et al., referenced above.

Figure 1B:
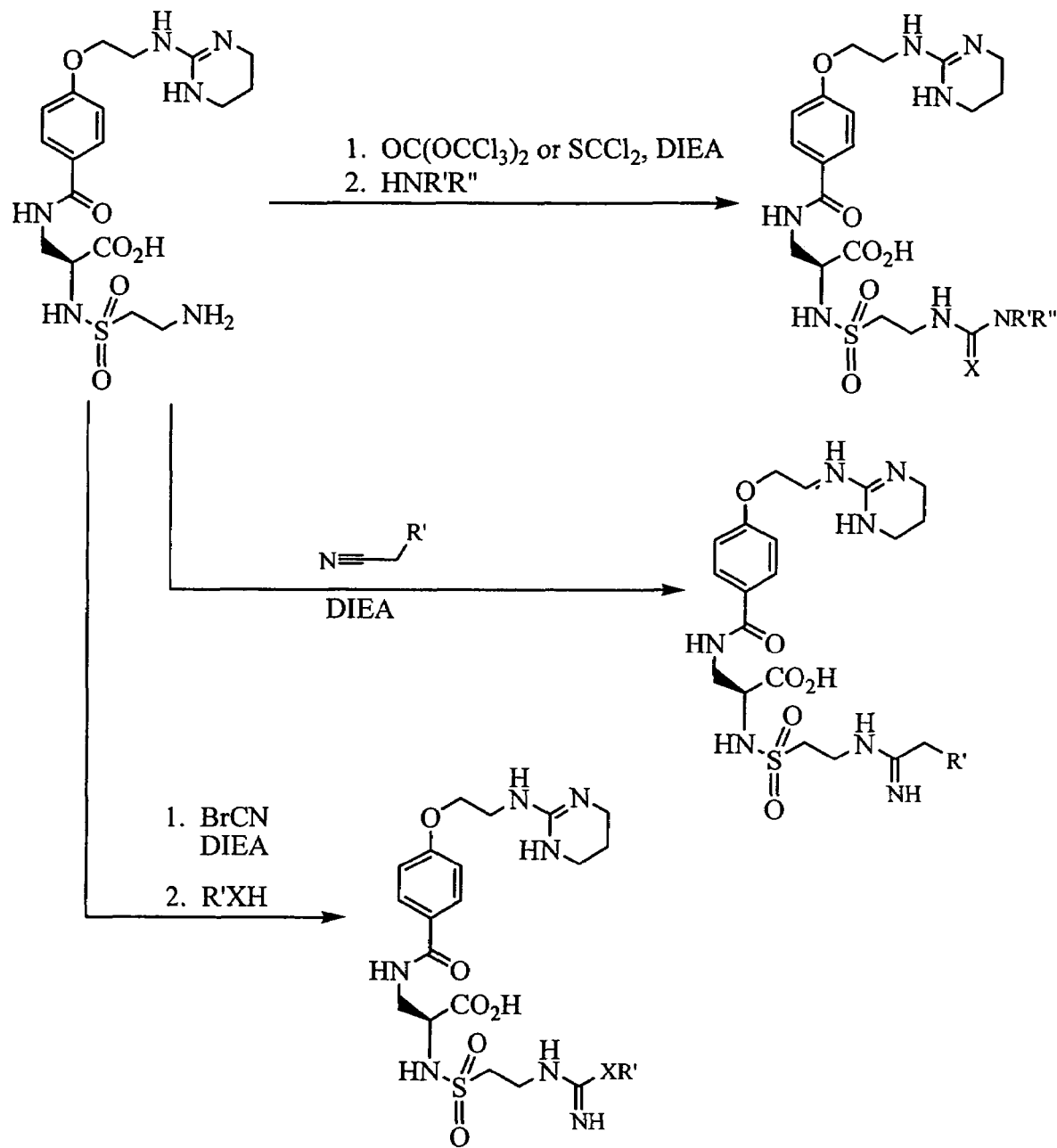
FIG. 1b illustrates synthetic routes to additional compounds within the scope of the invention.
Figure 2A:
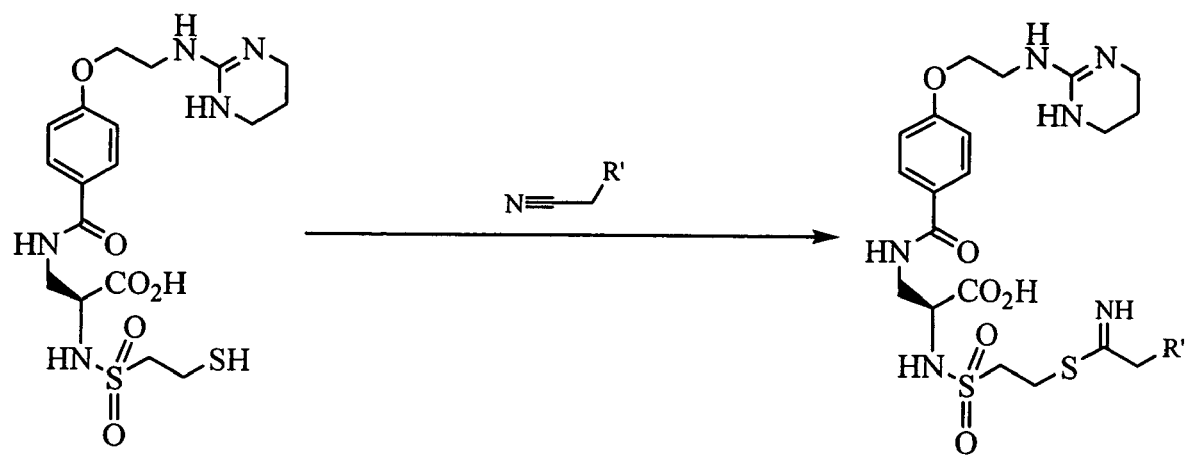
FIG. 2a illustrates a synthetic route to still further compounds within the scope of the invention.
Figure 2B:
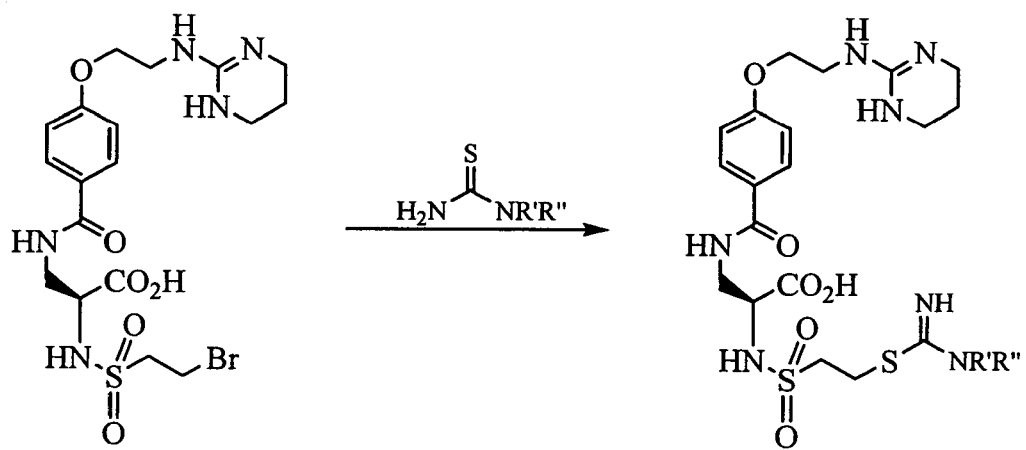
FIG. 2b illustrates a synthetic route to still further compounds within the scope of the invention.
Figure 2C:
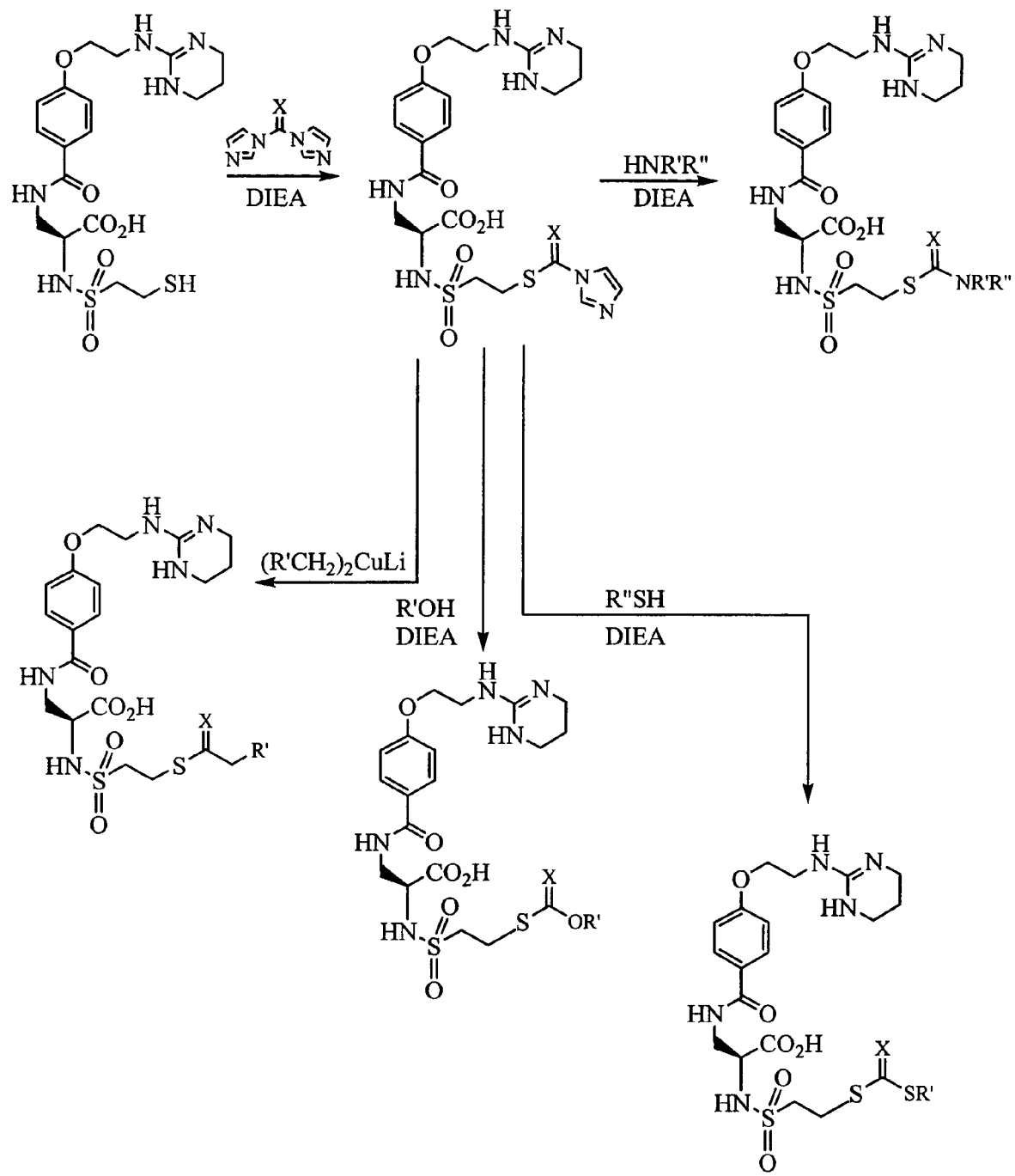
FIG. 2c illustrates synthetic routes to still further compounds within the scope of the invention.
Figure 3A:
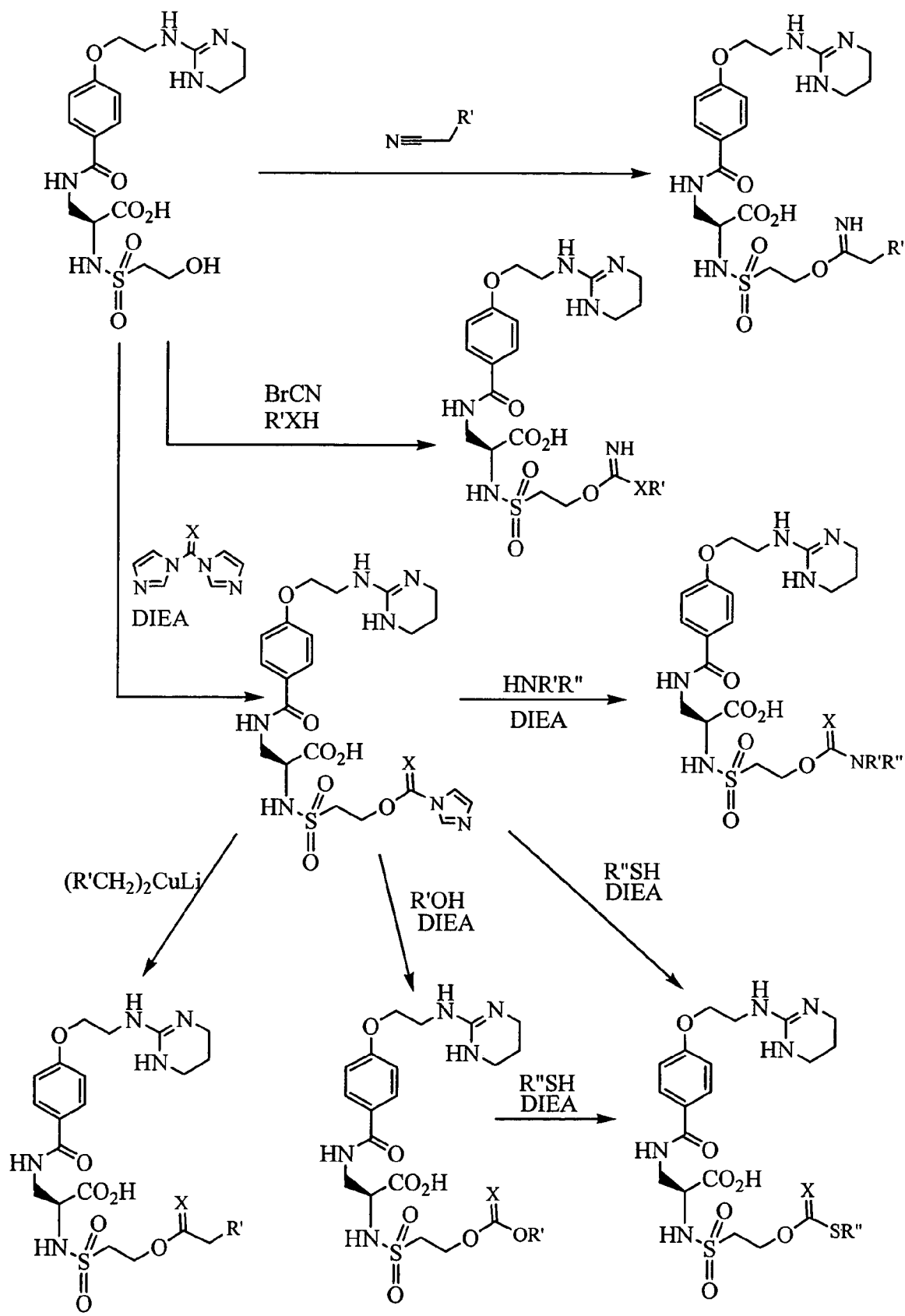
FIG. 3a illustrates synthetic routes to still further compounds within the scope of the invention.
Figure 3B:
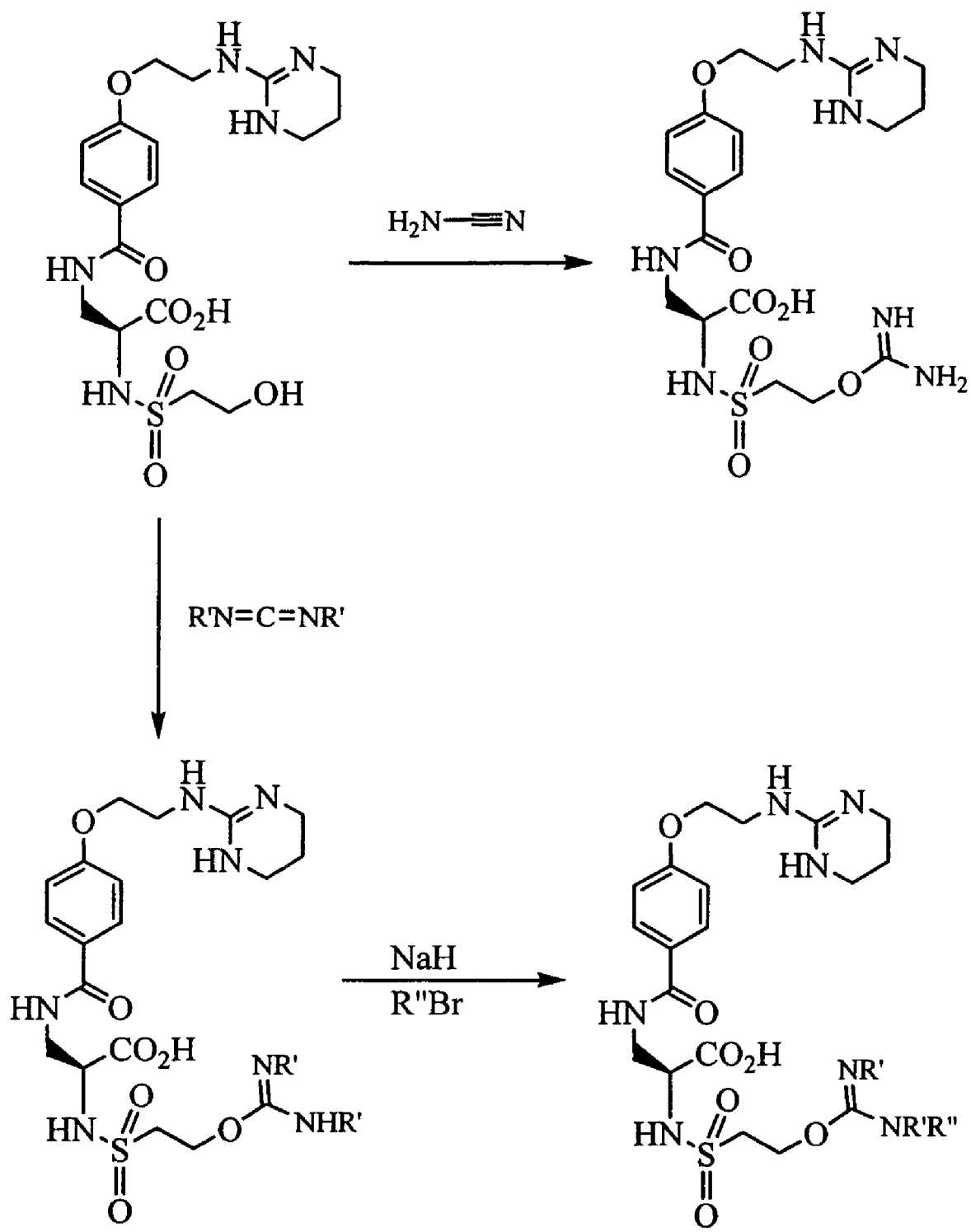
FIG. 3b illustrates synthetic routes to still further compounds within the scope of the invention.
Figure 4A:
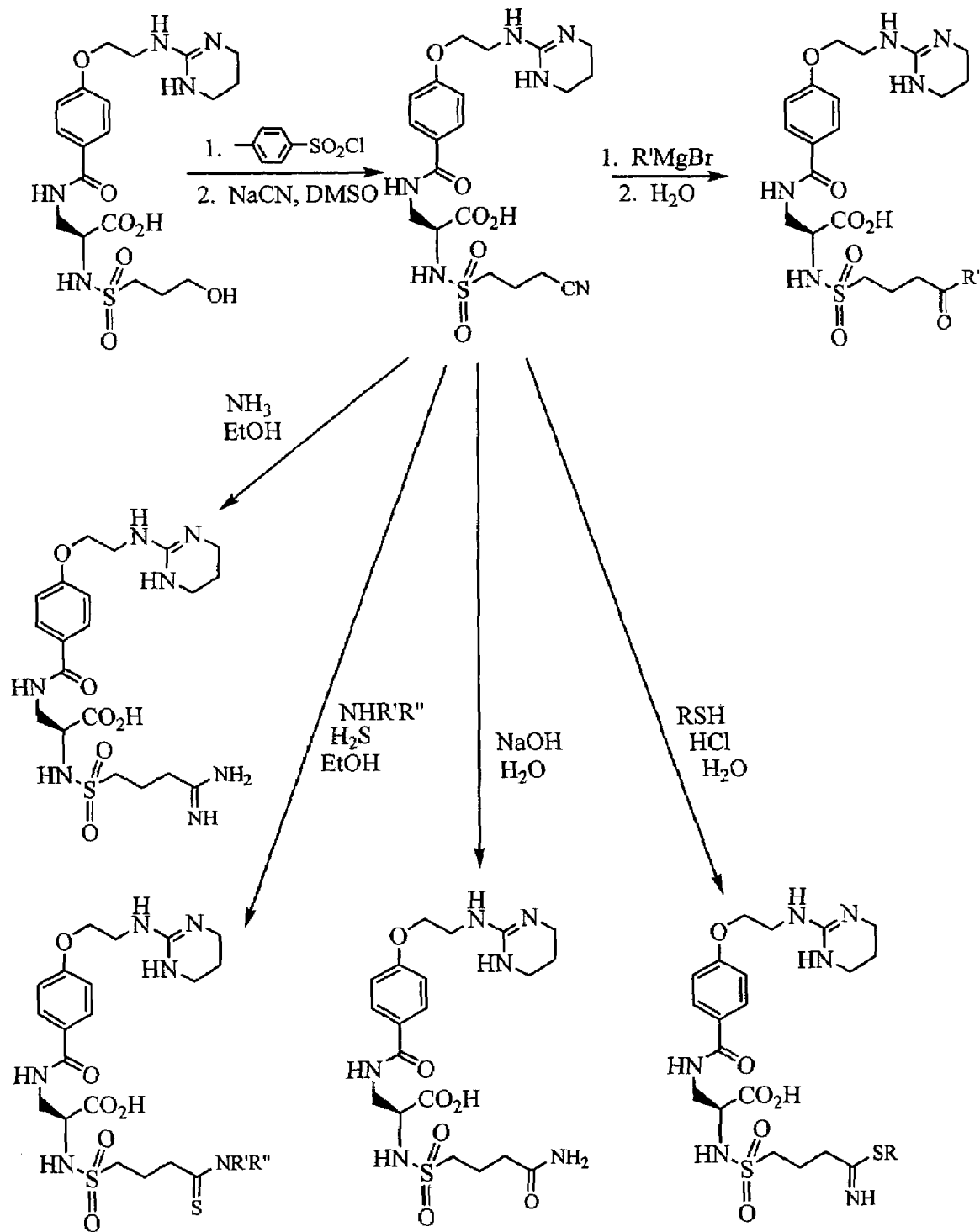
FIG. 4a illustrates synthetic routes to still further compounds within the scope of the invention.
Figure 4B:
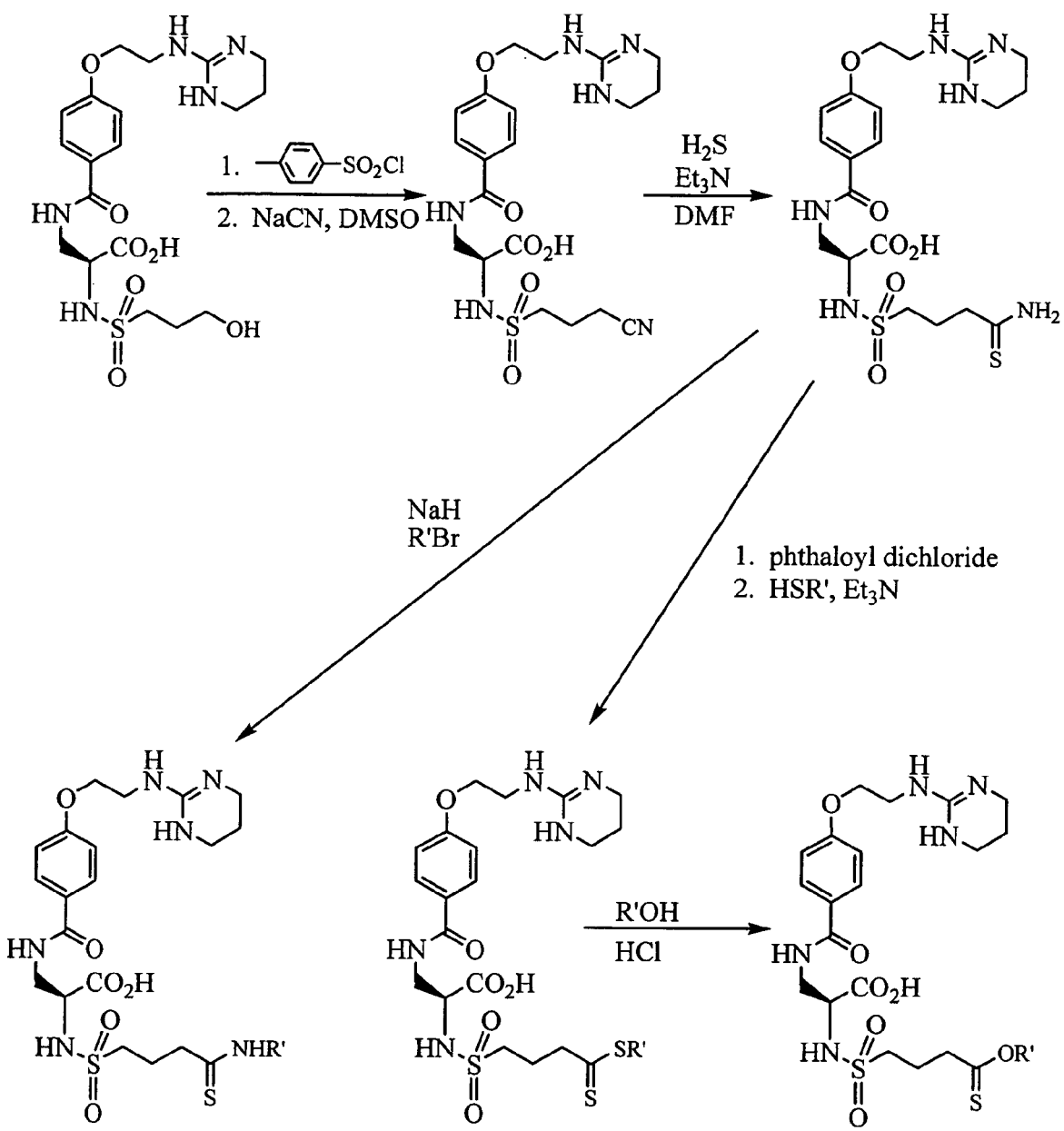
FIG. 4b illustrates synthetic routes to still further compounds within the scope of the invention.
Figure 4C:
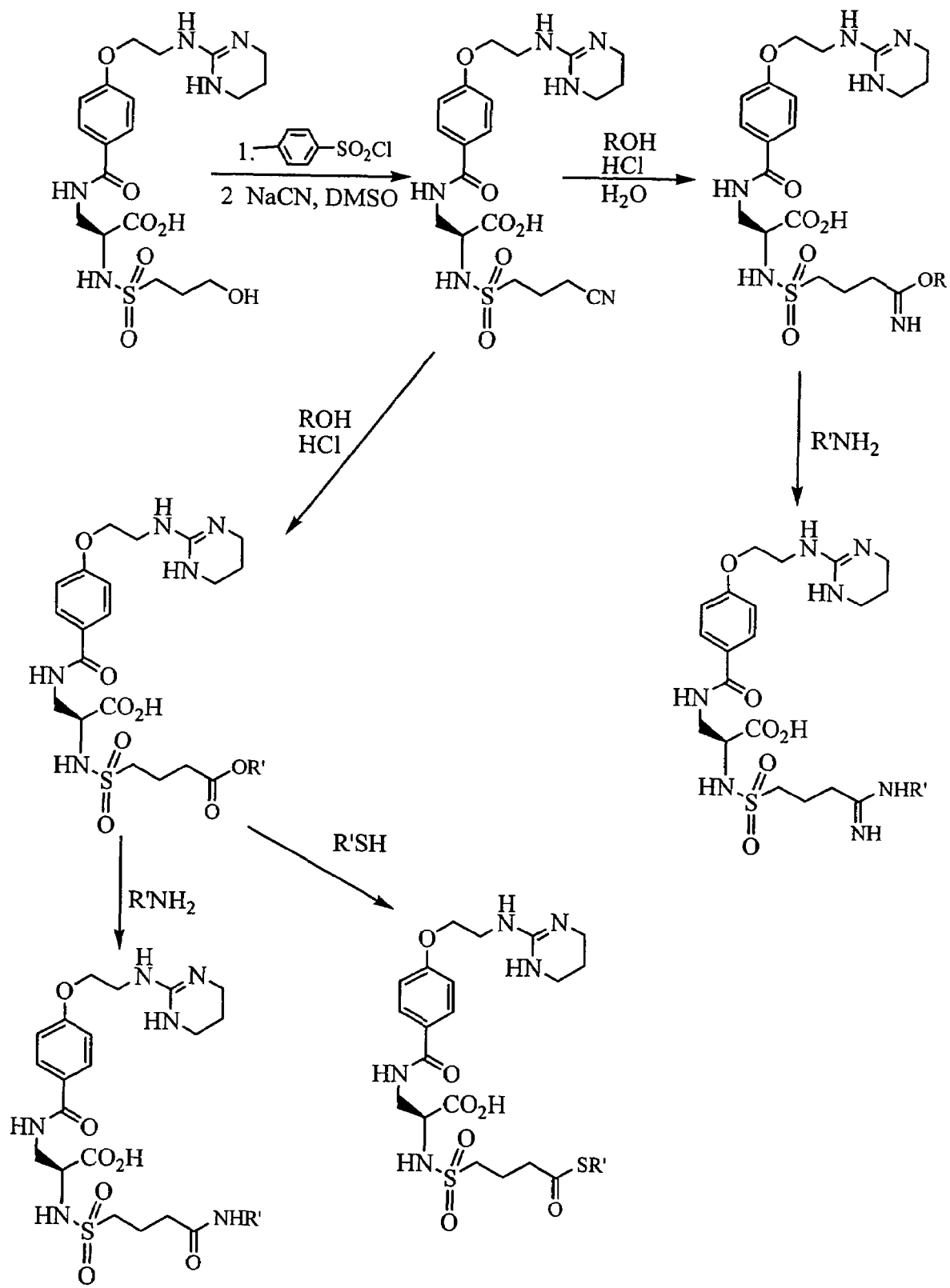
FIG. 4c illustrates synthetic routes to still further compounds within the scope of the invention.

Other synthesis procedures for compounds of this invention, or for precedessors from which compounds of this invention are readily prepared, are shown in the figures. The symbols in these figures do not correspond to the same symbols in the generic formula above but instead correspond to groups at the same site on the structure—the symbol X in the figures generally represents S or O, and the symbols R' and R'' in the figures generally represent alkyl, aryl, and various substituted alkyls and aryls. FIGS. 1a and 1b illustrate several alternate routes to compounds of the invention (or their immediate predecessors) in which $R^1$ is NH, starting from the Hood et al. compound, 4-[2-(3,4,5,6-tetrahydropyrimidin-2-ylamino)ethyloxy]benzoyl-2-(S)-aminoethylsulfonylamino-β-alanine. FIGS. 2a, 2b, and 2c illustrate several alternate routes to compounds of the invention (and their immediate predecessors) in which $R^1$ is S, starting from 4-[2-(3,4,5,6-tetrahydropyrimidin-2-ylamino)-ethyloxy] benzoyl-2-mercaptoethylsulfonylamino-β-alanine and 4-[2-(3,4,5,6-tetrahydropyrimidin-2-ylamino)ethyloxy]benzoyl-2-bromoethylsulfonylamino-β-alanine. FIGS. 3a and 3b illustrate several alternate routes to compounds of the invention (or their immediate predecessors) in which $R^1$ is O, starting from 4-[2-(3,4,5,6-tetrahydropyrimidin-2-ylamino) ethyloxy]benzoyl-2-hydroxyethylsulfonylamino-β-alanine. FIGS. 4a, 4b, and 4c illustrate several alternate routes to compounds of the invention (and their immediate predecessors) in which $R^1$ is $CH_2$, starting from 4-[2-(3,4,5,6-tetrahydropyrimidin-2-ylamino)ethyloxy]benzoyl-2-hydroxypropylsulfonylamino-β-alanine. The reagents and solvents indicated in the figures are represented by abbreviations that are conventional to synthesis chemists, i.e., DIEA denotes N,N-diisopropylethanolamine, DMSO denotes dimethylsulfoxide, EtOH denotes ethanol, and $Et_3N$ denotes triethylamine.

Synthesis examples of specific compounds within the scope of the invention are presented below, followed by test data showing the efficacy of the compounds for the various uses described herein.

EXAMPLE 1

Synthesis of 4-[2-(3,4,5,6-Tetrahydropyrimidin-2-ylamino)ethyloxy]benzoyl-2-(S)-[N-(3-butyloxycarbonylamino-neopenta-1-carbamyl)]-aminoethylsulfonylamino-β-alanine

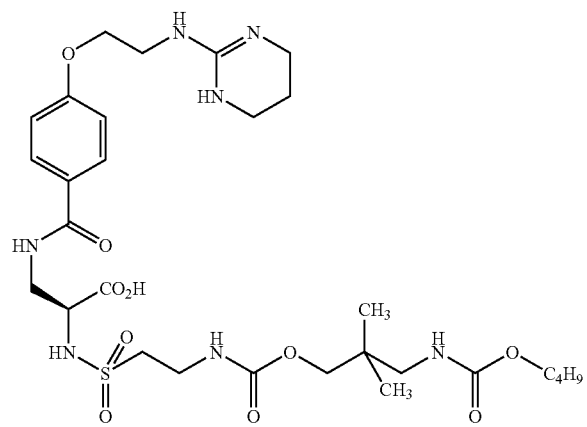

($R^1$=NH, X=O, $R^2$=O, $R^3$=$CH_3$, $R^4$=$CH_3$, n=1, $R^5$=NH, and $R^6$=C(=O)—O—$C_4H_9$)

3-(Boc-amino)-neopentyl-1-O-carbonylimidazole from N-Boc-amino-neopentyl alcohol. To a stirred solution of N-Boc-amino-neopentyl alcohol (2.00 g, 9.85 mmol) in anhydrous $CH_2Cl_2$ (8 mL) was added N,N-diisopropylethylamine (1.7 mL, 9.85 mmol) under argon. To this solution was added 1,1'-carbonyldiimidazole (2.80 g, 17.3 mmol) in $CH_2Cl_2$ (22 mL) as a slurry and the resulting mixture was stirred at room temperature for three hours. The mixture was then diluted to 50 mL with $CH_2Cl_2$, cooled to 0° C., and washed with ice-cold water (2×50 mL). The solvent was dried over $Na_2SO_4$, evaporated under reduced pressure, and dried under high vacuum to give 3-(Boc-amino)-neopentyl-1-O-carbonylimidazole (2.72 g, 9.16 mmol, 93%) as a white solid. The structure was confirmed as that of 3-(Boc-amino)-neopentyl-1-O-carbonylimidazole by the following. IR (KBr, $cm^{-1}$) 3367w, 3142m, 1759s, 1709s, 1474s, 1303s, 1179s, 1006m. $^1$H NMR (300 MHz, DMSO-$d_6$): 8.28 (s, 1H), 7.61 (s, 1H), 7.08 (s, 1H), 7.00 (t, J=6.4 Hz, 1H), 4.04 (s, 2H), 2.95 (d, J=6.4 Hz, 2H), 1.35 (s, 9H), 0.92 (s, 6H). $^{13}$C NMR (75 MHz, DMSO-$d_6$): 156.5, 148.8, 137.7, 130.6, 117.9, 78.0, 73.6, 47.2, 36.0, 28.6, 22.6.

4-[2-(3,4,5,6-Tetrahydropyrimidin-2-ylamino)ethyloxy] benzoyl-2-(S)-[N-(3-butyloxycarbonylamino-neopenta-1-carbamyl)]-aminoethylsulfonylamino-β-alanine from 3-(Boc-amino)-neopentyl-1-O-carbonylimidazole. To a mixture of 3-(Boc-amino)-neopentyl-1-O-carbonylimidazole (0.42 g, 1.42 mmol) in anhydrous DMSO (12 mL) under argon was added (0.50 g, 1.02 mmol) of 4-[2-(3,4,5,6-tetrahydropyrimidin-2-ylamino)-ethyloxy]benzoyl-2-(S)-aminoethylsulfonylamino-O-alanine, as the hydrochloride salt, followed by addition of N,N-diisopropylethylamine (0.53 mL, 3.05 mmol). The mixture was stirred under argon at 70° C. for 18 hours. Excess solvent was removed by rotary evaporation and the remaining residue was washed first with water (2×5 mL) and then with ethyl acetate (2×3 mL). The remaining solid was dissolved in hot ethanol, then cooled, and the resulting precipitate was collected by vacuum filtration, then dried under high vacuum to give an off-white solid. The structure was confirmed as that of 4-[2-(3,4,5,6-tetrahydropyrimidin-2-ylamino)ethyloxy]benzoyl-2-(S)-[N-(3-butyloxycarbonylamino-neopenta-1-carbamyl)]-aminoethylsulfonylamino-3-alanine (0.65 g, 0.95 mmol, 66%) by the following. IR (KBr, $cm^{-1}$) 3323s, 3051m, 2973s, 2884m, 1704s, 1650s, 1607s, 1533m, 1505s, 1319s, 1146s, 1057m. $^1$H NMR (300 MHz, DMSO-$d_6$): 8.86 (br, 1H), 8.58 (br, 2H), 8.29 (br, 1H), 7.73 (d, J=8.6 Hz, 2H), 7.29 (t, J=5.3 Hz, 1H), 7.02 (br, 1H), 6.92 (d, J=8.6 Hz, 2H), 6.79 (t, J=5.8 Hz, 1H), 4.04 (t, J=4.8 Hz, 2H), 3.73 (m, 1H), 3.67 (s, 2H), 3.55 (m, 2H), 3.47 (m, 2H), 3.37 (t, J=7.0 Hz, 2H), 3.24 (br, 4H), 3.18 (m, 2H), 2.82 (d, J=5.8 Hz, 2H), 1.80 (m, 2H), 1.37 (s, 9H), 0.79 (s, 6H). $^{13}$C NMR (75 MHz, DMSO-$d_6$): 173.5, 165.8, 160.8, 156.8, 156.5, 153.6, 129.2, 127.7, 114.5, 77.9, 70.5, 66.5, 56.6, 51.8, 47.5, 43.3, 38.4, 36.2, 35.9, 28.7, 22.6, 20.2, 15.6. MS (FAB, NBA): m/z 686 (100, [M+H]$^+$). HR-MS (FAB, NBA): m/z 686.3181 ([M+H]$^+$, $C_{29}H_{48}N_7O_{10}S$, calcd 686.3184).

EXAMPLE 2

Synthesis of 4-[2-(3,4,5,6-Tetrahydropyrimidin-2-ylamino)ethyloxy]benzoyl-2-(S)-[N-(3-amino-neopenta-1-carbamyl)]-aminoethylsulfonylamino-β-alanine Hydrochloride

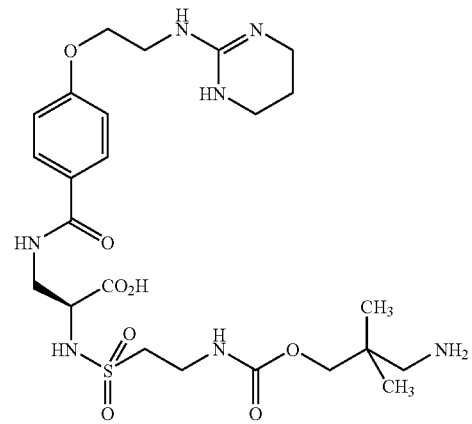

($R^1$=NH, X=O, $R^2$=O, $R^3$=$CH_3$, $R^4$=$CH_3$, n=1, $R^5$=NH, and $R^6$=H, Hydrochloride Salt)

This compound was prepared from the compound of Example 1 by the following procedure.

A mixture of the compound of Example 1 (0.10 g, 0.14 mmol) and 4M HCl in dioxane (50 mL) was stirred under argon at 0° C. for 3 hours. The resulting heterogeneous mixture was frozen at −80° C., then lyophilized to dryness to give the title compound in quantitative yield as a hydrochloride salt. The molecular structure was confirmed by the following. $^1$H NMR (300 MHz, DMSO-$d_6$): 12.97 (br, 1H), 8.49 (br, 1H), 7.99 (br, 2H), 7.95 (br, 2H), 7.88 (br, 1H), 7.84 (d, J=8.3 Hz, 2H), 7.60 (t, J=5.1 Hz, 1H), 7.40 (t, J=5.0 Hz, 1H), 7.02 (d, J=8.3 Hz, 2H), 4.12 (t, J=6.4 Hz, 2H), 3.79 (s, 2H), 3.70 (m, 1H), 3.53 (m, 2H), 3.51 (br, 2H), 3.48 (m, 2H), 3.26 (br, 4H), 3.17 (m, 2H), 2.70 (br, 2H), 1.82 (m, 2H), 0.94 (s, 6H). MS (FAB, NBA): m/z 586 (100, [M+H]$^+$). HR-MS (FAB, NBA): m/z 586.2657 ([M+H]$^+$, $C_{24}H_{40}N_7O_8S$, calcd 586.2659).

EXAMPLE 3

Synthesis of 4-[2-(3,4,5,6-Tetrahydropyrimidin-2-ylamino)ethyloxy]benzoyl-2-(S)-[N-(3-butyloxycarbonylamino-ethyl-1-carbamyl)]-aminoethylsulfonylamino-β-alanine

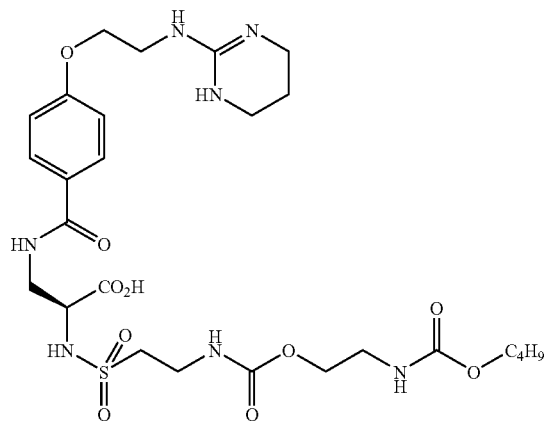

($R^1$=NH, X=O, $R^2$=O, n=0, $R^5$=NH, and $R^6$=C(=O)—O—$C_4H_9$)

2-(Boc-amino)-ethyl-1-O-carbonylimidazole from N-Boc-aminoethanol. The procedure of Example 1, first paragraph, was repeated, except substituting N-Boc-aminoethanol for N-Boc-amino-neopentyl alcohol. The product was a white solid (yield 90%), whose structure was confirmed as that of 2-(Boc-amino)-ethyl-1-O-carbonylimidazole by the following. IR (KBr, cm$^{-1}$) 3403s, 2980m, 1748s, 1713s, 1526s, 1322s, 1166s, 1006m. $^1$H NMR (300 MHz, DMSO-$d_6$): 8.27 (s, 1H), 7.61 (s, 1H), 7.15 (t, J=5.7 Hz, 1H), 7.07 (s, 1H), 4.33 (t, J=5.1 Hz, 2H), 3.33 (m, 2H), 1.36 (s, 9H). $^{13}$C NMR (75 MHz, CDCl$_3$): 155.8, 148.6, 137.2, 130.7, 117.2, 80.0, 67.4, 39.4, 28.3.

4-[2-(3,4,5,6-Tetrahydropyrimidin-2-ylamino)ethyloxy]benzoyl-2-(S)-[N-(2-butyloxycarbonylamino-ethyl-1-carbamyl)]-aminoethylsulfonylamino-β-alanine from 2-(Boc-amino)-ethyl-1-O-carbonylimidazole. The procedure of Example 1, second paragraph, was followed, except substituting 2-(Boc-amino)-ethyl-1-O-carbonylimidazole for 2-(Boc-amino)-neopentyl-1-O-carbonylimidazole. The product was a white powder (yield 23%), whose structure was confirmed as that of 4-[2-(3,4,5,6-tetrahydropyrimidin-2-ylamino)ethyloxy]benzoyl-2-(S)-[N-(2-butyloxycarbonylamino-ethyl-1-carbamyl)]-aminoethylsulfonylamino-3-alanine by the following. IR (KBr, cm$^{-1}$) 3380s, 3048w, 2976m, 2886w, 1702s, 1652s, 1607s, 1529m, 1367m, 1254s, 1056m. $^1$H NMR (300 MHz, DMSO-$d_6$): 8.73 (br, 1H), 8.48 (br, 2H), 8.35 (br, 1H), 7.72 (d, J=8.6 Hz, 2H), 7.36 (t, J=5.9 Hz, 1H), 6.96 (br, 1H), 6.92 (d, J=8.6 Hz, 2H), 6.90 (t, J=5.8 Hz, 1H), 4.04 (t, J=5.3 Hz, 2H), 3.91 (t, J=5.5 Hz, 2H), 3.63 (m, 1H), 3.55 (m, 2H), 3.47 (m, 2H), 3.34 (br, 2H), 3.24 (br, 4H), 3.16 (m, 2H), 3.11 (m, 2H), 1.81 (m, 2H), 1.37 (s, 9H). MS (FAB, NBA): m/z 644 (100, [M+H]$^+$). HR-MS (FAB, NBA): m/z 644.2716 ([M+H]$^+$, $C_{26}H_{42}N_7O_{10}S$, calcd 644.2714).

EXAMPLE 4

Synthesis of 4-[2-(3,4,5,6-Tetrahydropyrimidin-2-ylamino)ethyloxy]benzoyl-2-(S)-[N-(3-amino-ethyl-1-carbamyl)]-aminoethylsulfonylamino-β-alanine

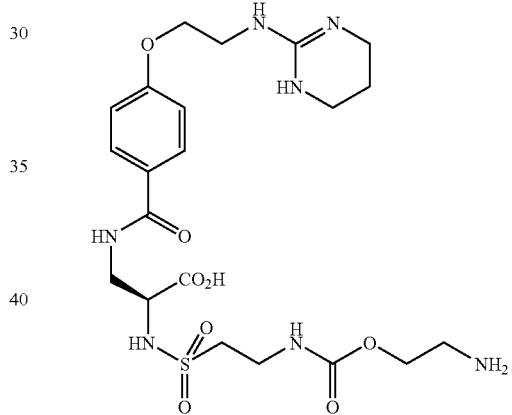

($R^1$=NH, X=O, $R^2$=O, n=0, $R^5$=NH, and $R^6$=H, Hydrochloride Salt)

This compound was prepared from the compound of Example 3 by the following procedure.

A mixture of the compound of Example 3 (0.14 mmol) and 4M HCl in dioxane (50 mL) was stirred under argon at 0° C. for 3 hours. The resulting heterogeneous mixture was frozen at −80° C., then lyophilized to dryness to give the title compound in quantitative yield as a hydrochloride salt. The molecular structure was confirmed by the following. $^1$H NMR (300 MHz, DMSO-$d_6$): 12.97 (br, 1H), 8.50 (br, 1H), 8.06 (br, 2H), 7.97 (br, 2H), 7.90 (br, 1H), 7.84 (d, J=8.7 Hz, 2H), 7.59 (t, J=5.5 Hz, 1H), 7.21 (t, J=5.0 Hz, 1H), 7.02 (d, J=8.7 Hz, 2H), 4.14 (br, 2H), 4.12 (br, 2H), 3.70 (m, 1H), 3.53 (m, 2H), 3.51 (br, 2H), 3.49 (m, 2H), 3.26 (br, 4H), 3.17 (m, 2H), 3.03 (m, 2H), 1.82 (m, 2H). MS (FAB, NBA): m/z 544 (100, [M+H]$^+$). HR-MS (FAB, NBA): m/z 544.2187 ([M+H]$^+$, $C_{21}H_{34}N_7O_8S$, calcd 544.2189).

EXAMPLE 5

Synthesis of 4-[2-(3,4,5,6-Tetrahydropyrimidin-2-ylamino)ethyloxy]benzoyl-2-(S)-[N-(3-butyloxycarbonylamino-propyl-1-carbamyl)]-aminoethylsulfonylamino-β-alanine

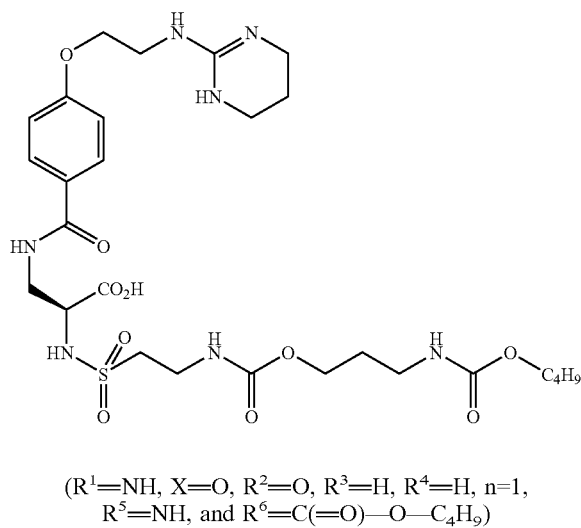

($R^1$=NH, X=O, $R^2$=O, $R^3$=H, $R^4$=H, n=1,
$R^5$=NH, and $R^6$=C(=O)—O—$C_4H_9$)

2-(Boc-amino)-propyl-1-O-carbonylimidazole from N-Boc-aminopropanol. The procedure of Example 1, first paragraph, was repeated, except using N-Boc-aminopropanol in place of N-Boc-amino-neopentyl alcohol. The product was a white solid (yield 92%), whose structure was confirmed as that of 2-(Boc-amino)-propyl-1-O-carbonylimidazole by the following. IR (KBr, cm$^{-1}$) 3337s, 3141m, 2977m, 1753s, 1721s, 1520s, 1415m, 1160s, 1016m. $^1$H NMR (300 MHz, DMSO-d$_6$): 8.27 (s, 1H), 7.60 (s, 1H), 7.08 (s, 1H), 6.94 (t, J=5.5 Hz, 1H), 4.37 (t, J=6.2 Hz, 2H), 3.09 (m, 2H), 1.84 (m, 2H), 1.35 (s, 9H). $^{13}$C NMR (75 MHz, CDCl$_3$): 155.9, 148.7, 137.1, 130.5, 117.1, 79.5, 66.0, 37.1, 29.2, 28.3.

4-[2-(3,4,5,6-Tetrahydropyrimidin-2-ylamino)ethyloxy]benzoyl-2-(S)-[N-(2-butyloxycarbonylamino-propyl-1-carbamyl)]-aminoethylsulfonylamino-β-alanine from 2-(Boc-amino)-propyl-1-O-carbonylimidazole. The procedure of Example 1, second paragraph, was followed, except using 2-(Boc-amino)-propyl-1-O-carbonylimidazole instead of 2-(Boc-amino)-neopentyl-1-O-carbonylimidazole. The product was a white powder (yield 36%), whose structure was confirmed as that of 4-[2-(3,4,5,6-tetrahydropyrimidin-2-ylamino)ethyloxy]benzoyl-2-(S)-[N-(2-butyloxycarbonylamino-propyl-1-carbamyl)]-aminoethylsulfonylamino-3-alanine by the following. IR (KBr, cm$^{-1}$) 3380s, 2976m, 2928m, 2881w, 1687m, 1647s, 1607s, 1504s, 1367m, 1255s, 1178m, 1054w. $^1$HNMR(300 MHz, DMSO-d$_6$): 9.07 (br, 1H), 8.67 (br, 2H), 8.28 (br, 1H), 7.72 (d, J=8.6 Hz, 2H), 7.34 (t, J=5.3 Hz, 1H), 7.01 (br, 1H), 6.90 (d, J=8.6 Hz, 2H), 6.85 (t, J=5.5 Hz, 1H), 4.02 (t, J=4.6 Hz, 2H), 3.92 (t, J=6.2 Hz, 2H), 3.67 (m, 1H), 3.55 (m, 2H), 3.47 (m, 2H), 3.34 (br, 2H), 3.23 (br, 4H), 3.18 (m, 2H), 2.96 (m, 2H), 1.80 (m, 2H), 1.63 (m, 2H), 1.37 (s, 9H). $^{13}$C NMR (75 MHz, DMSO-d$_6$): 173.7, 165.7, 160.7, 156.6, 156.0, 153.7, 129.2, 127.7, 114.5, 78.0, 66.5, 62.3, 56.7, 51.6, 43.5, 38.4, 37.3, 35.9, 29.7, 28.7, 20.2 (21 of 22 resonances observed). MS (FAB, NBA): m/z 658 (100, [M+H]$^+$). HR-MS (FAB, NBA): m/z 658.2872 ([M+H]$^+$, $C_{27}H_{44}N_7O_{10}S$, calcd 658.2870).

EXAMPLE 6

Synthesis of 4-[2-(3,4,5,6-Tetrahydropyrimidin-2-ylamino)ethyloxy]benzoyl-2-(S)-[N-(3-amino-propyl-1-carbamyl)]-aminoethylsulfonylamino-β-alanine

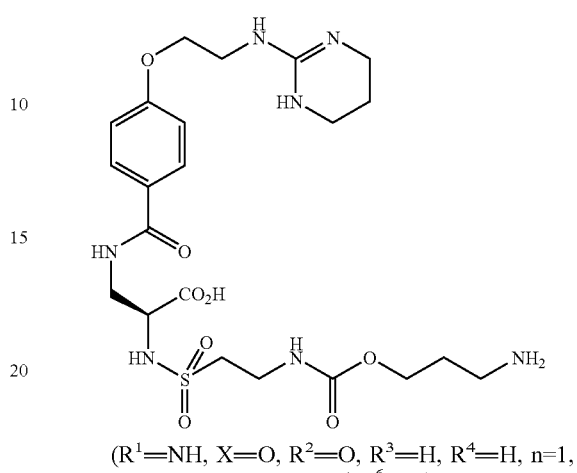

($R^1$=NH, X=O, $R^2$=O, $R^3$=H, $R^4$=H, n=1,
R=NH, and $R^6$=H)

This compound was prepared from the compound of Example 5 by the following procedure.

A mixture of the compound of Example 5 (0.14 mmol) and 4M HCl in dioxane (50 mL) was stirred under argon at 0° C. for 3 hours. The resulting heterogeneous mixture was frozen at −80° C. then lyophilized to dryness to give the title compound in quantitative yield as a hydrochloride salt. The molecular structure was confirmed by the following. $^1$H NMR MHz, DMSO-d$_6$): 12.96 (br, 1H), 8.50 (br, 1H), 7.95 (br, 2H), 7.91 (br, 2H), 7.87 (br, 1H), 7.83 (d, J=8.6 Hz, 2H), 7.57 (t, J=5.1 Hz, 1H), 7.29 (t, J=4.9 Hz, 1H), 7.02 (d, J=8.6 Hz, 2H), 4.12 (t, J=4.7 Hz, 2H), 4.01 (t, J=5.5 Hz, 2H), 3.70 (m, 1H), 3.55 (m, 2H), 3.50 (br, 2H), 3.48 (m, 2H), 3.26 (br, 4H), 3.15 (m, 2H), 2.84 (m, 2H), 1.84 (m, 2H), 1.82 (m, 2H). MS (FAB, NBA): m/z 558 (100, [M+H]$^+$). HR-MS (FAB, NBA): m/z 558.2344 ([M+H]$^+$, $C_{22}H_{36}N_7O_8S$, calcd 558.2346).

EXAMPLE 7

Synthesis of 4-[2-(3,4,5,6-Tetrahydropyrimidin-2-ylamino)ethyloxy]benzoyl-2-(S)-[N-(3-butyloxycarbonylamino-butyl-1-carbamyl)]-aminoethylsulfonylamino-β-alanine

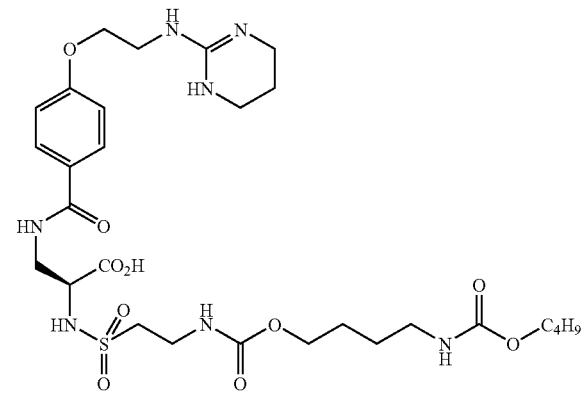

($R^1$=NH, X=O, $R^2$=O, $R^3$=H, $R^4$=H, n=2,
$R^5$=NH, and $R^6$=C(=O)—O—$C_4H_9$)

2-(Boc-amino)-butyl-1-O-carbonylimidazole from N-Boc-aminobutanol. The procedure of Example 1, first paragraph, was repeated, except using N-Boc-aminobutanol in place of N-Boc-amino-neopentyl alcohol. The product was a clear oil (yield 90%), whose structure was confirmed as that of 2-(Boc-amino)-butyl-1-O-carbonylimidazole by the following. IR (KBr, cm$^{-1}$) 3407s, 2976m, 2934m, 1764s, 1712s, 1526s, 1475m, 1283s, 1174s, 1004m. $^1$H NMR (300 MHz, DMSO-d$_6$): 8.26 (s, 1H), 7.60 (s, 1H), 7.08 (s, 1H), 6.84 (t, J=5.8 Hz, 1H), 4.37 (t, J=6.3 Hz, 2H), 2.97 (m, 2H), 1.72 (m, 2H), 1.51 (m, 2H), 1.37 (s, 9H). $^{13}$C NMR (75 MHz, DMSO-d$_6$): 156.1, 148.8, 137.6, 130.1, 117.9, 77.9, 68.3, 38.6, 28.7, 26.1, 25.7.

4-[2-(3,4,5,6-Tetrahydropyrimidin-2-ylamino)ethyloxy]benzoyl-2-(S)-[N-(2-butyloxycarbonylamino-butyl-1-carbamyl)]-aminoethylsulfonylamino-β-alanine from 2-(Boc-amino)-butyl-1-O-carbonylimidazole. The procedure of Example 1, second paragraph, was followed, except using 2-(Boc-amino)-butyl-1-O-carbonylimidazole instead of 2-(Boc-amino)-neopentyl-1-O-carbonylimidazole. The product was an off-white powder (yield 33%), whose structure was confirmed as that of 4-[2-(3,4,5,6-tetrahydropyrimidin-2-ylamino)ethyloxy]benzoyl-2-(S)-[N-(2-butyloxycarbonylamino-butyl-1-carbamyl)]-aminoethylsulfonylamino-3-alanine by the following. IR (KBr, cm$^{-1}$) 3380s, 3051w, 2975m, 2935m, 2874m, 1687m, 1647s, 1607s, 1504s, 1366m, 1255s, 1148m, 1055m. $^1$H NMR (300 MHz, DMSO-d$_6$): 9.06 (br, 1H), 8.66 (br, 2H), 8.28 (br, 1H), 7.72 (d, J=8.2 Hz, 2H), 7.33 (t, J=5.1 Hz, 1H), 6.98 (br, 1H), 6.90 (d, J=8.2 Hz, 2H), 6.83 (t, J=5.5 Hz, 1H), 4.02 (t, J=4.7 Hz, 2H), 3.91 (t, J=5.9 Hz, 2H), 3.66 (m, 1H), 3.55 (m, 2H), 3.46 (m, 2H), 3.41 (br, 2H), 3.23 (br, 4H), 3.18 (m, 2H), 2.90 (m, 2H), 1.80 (m, 2H), 1.49 (m, 2H), 1.47 (m, 2H), 1.36 (s, 9H). MS (FAB, NBA): m/z 672 (100, [M+H]$^+$). HR-MS (FAB, NBA): m/z 672.3029 ([M+H]$^+$, $C_{28}H_{46}N_7O_{10}S$, calcd 672.3027).

EXAMPLE 8

Synthesis of 4-[2-(3,4,5,6-Tetrahydropyrimidin-2-ylamino)ethyloxy]benzoyl-2-(S)-[N-(3-amino-butyl-1-carbamyl)]-aminoethylsulfonylamino-β-alanine

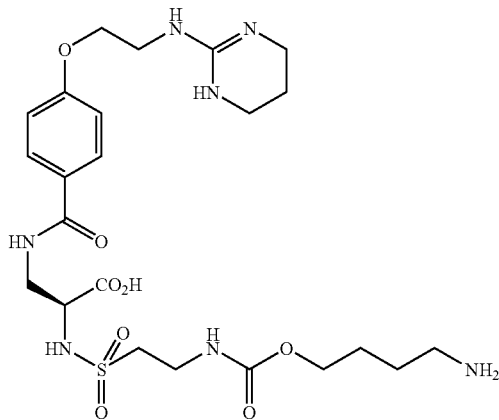

($R^1$=NH, X=O, $R^2$=O, $R^3$=H, $R^4$=H, n=2, $R^5$=NH, and $R^6$=H, Hydrochloride Salt)

This compound was prepared from the compound of Example 7 by the following procedure.

A mixture of the compound of Example 7 (0.14 mmol) and 4M HCl in dioxane (50 mL) was stirred under argon at 0° C. for 3 hours. The resulting heterogeneous mixture was frozen at –80° C. then lyophilized to dryness to give the title compound in quantitative yield as a hydrochloride salt. The molecular structure was confirmed by the following. $^1$H NMR MHz, DMSO-d$_6$): 12.96 (br, 1H), 8.50 (br, 1H), 8.02 (br, 2H), 7.95 (br, 2H), 7.88 (br, 1H), 7.84 (d, J=8.6 Hz, 2H), 7.63 (t, J=5.7 Hz, 1H), 7.22 (t, J=5.3 Hz, 1H), 7.01 (d, J=8.6 Hz, 2H), 4.12 (br, 2H), 3.95 (br, 2H), 3.68 (m, 1H), 3.54 (m, 2H), 3.51 (br, 2H), 3.48 (m, 2H), 3.26 (br, 4H), 3.15 (m, 2H), 2.79 (m, 2H), 1.81 (m, 2H), 1.66 (m, 2H), 1.61 (m, 2H). MS (FAB, NBA): m/z 572 (100, [M+H]$^+$). HR-MS (FAB, NBA): m/z 572.2507 ([M+H]$^+$, $C_{23}H_{38}N_7O_8S$, calcd 572.2502).

EXAMPLE 9

Receptor/Ligand Challenge Assay of Vitronectin to Integrin αvβ3 Receptor Antagonists in the Presence of Test Compounds The title compounds of Examples 1 through 8 were tested for their activity as αvβ3 receptor antagonists by the procedure described below, and the buffers, solutions, and reagents used in the procedure are listed following the procedure.

Procedure. Integrin protein $α_vβ_3$ (purchased from Chemicon International, Inc., Temecula, Calif., USA) was diluted to a final concentration of 1 μg/mL in coating buffer (2.1). The $α_vβ_3$ coating solution was applied to 96-well polystyrene microtiter plate at 100 μL/well. (A total of 10 mL is needed to coat one 96-well plate). The plates were then sealed and allowed to incubate at 4° C. for at least 8 hours. The coating solution was then removed and the plate was washed two times with 300 μL/well of washing solution (2.2). Blocking buffer (2.3) was then added in amounts of 150 μL/well and the plate was incubated at room temperature for 2 hours. The blocking buffer was then removed, and the integrin antagonistic substances (117 μL of 1.25 μM (in H$_2$O)) were added in quadruplicate to column 1 of the twelve well columns of the plate. For example, 117 μL of 1.25 μM 4-[2-(3,4,5,6-tetrahydropyrimidin-2 ylamino)ethyloxy]benzoyl-2-(S)-aminoethylsulfonylamino-β-alanine, the antagonist described by Hood et al. referenced above was added to column 1, rows A-D and 117 μL of 1.25 μM of the antagonist of Example 1 was added to column 1, rows E-F. Binding buffer (2.4) (80 μL) was added to the remaining wells of the plate (column 2-12, rows A-F). A multichannel pipet was used to transfer 37 μL aliquots of the solutions from column 1 to column 2. The solutions were then mixed in the column 2 wells by drawing them up and down in the pipet 15 times. Solutions (37 μL) were then transferred from column 2 to column 3 and mixed by being drawn up and down in the pipet 15 times. The process was repeated across the columns to column 12, and the last 37 μL of solution was discarded. Biotinylated Vitronectin solution (2.5) was then added (20 μL/well, 0.1 μg/well). The final volume was 100 μL total per well, and the concentrations (nM) of analytes in columns 1-12 respectively were as follows: 1000, 316, 100, 31.6, 10.0, 3.16, 1.00, 0.316, 0.100, 0.0316, 0.01, and 0.00316.

The plate was agitated for thorough mixing of the solutions, then covered and incubated at room temperature for 3 hours. The solutions were then discarded and the plate was washed 3 times with 170 μL/well of washing solution (2.2). NeutrAvidin-HRP solution (2.6) was then added (100 μL/well, 0.01 μg/well), cover, and the plate was incubated at room temperature for 30 minutes. The solutions in the wells were then discarded and the plate was washed 3 times with 170 μL/well of washing solution (2.2). Chemiluminescent Substrate solution (2.7) was then added to the plate (100 μL/well), and the luminescence was read using the Wallac Victor 1420 Multilabel Counter (PerkinElmer, Inc., Boston, Mass., USA). A plot of average luminescence vs. concentration was generated using KaleidaGraph (version 3.5) software and the $IC_{50}$ values were calculated using the following formula: Max−Max*M0^m1/(m2^m1+M0^m1); m1=1;m2=1, where Max is the maximum luminescence observed.

The results are expressed in the table below, both in terms of the 50% inhibitory concentration ($IC_{50}$) of each test compound and the ratio of 50% inhibitory concentration ($IC_{50}$) of the test compound to that of the Hood et al. antagonist 4-[2-(3,4,5,6-tetrahydropyrimidin-2-ylamino) ethyloxy]benzoyl-2-(S)-aminoethylsulfonylamino-β-alanine.

Buffers and Solutions:

| | |
|---|---|
| 2.1 Coating Buffer | In redistilled water, 50 mM Tris (Trizma Base from Sigma-Aldrich), 150 mM NaCl, 1 mM $CaCl_2$, 1 mM $MgCl_2$, 1 mM $MnCl_2$, pH = 7.4. |
| 2.2 Washing Solution | 1 to 25 dilution in water of Wash Concentrate (from DELFIA) |
| 2.3 Blocking Buffer | 1 to 20 dilution in water of Milk Diluent/Blocking Solution Concentrate (from KPL, Inc., Gaithersburg, Maryland, USA) |
| 2.4 Binding Buffer | Mixture of 90% coating buffer (2.1) and 10% blocking buffer (2.3). |
| 2.5 Biotinylated Vitronectin Solution | 17.5 μL of 0.714 μg/μL solution of Biotinylated Vitronectin (3.1) is diluted with 2.5 mL of binding buffer (2.4) to a final concentration of 5 μg/mL. |
| 2.6 NeutrAvidin-HRP Solution | 15 μL of 0.1 μg/μL solution of NeutrAvidin-HRP (3.2) is diluted with 15 mL of binding buffer (2.4) to a final concentration of 0.1 μg/mL. |
| 2.7 Chemiluminescent Substrate Solution | Equal volume mixture of LumiGLO Substrate A and LumiGLO Substrate B (from KPL, Inc.). |

3. Reagents:

| | |
|---|---|
| 3.1 0.714 μg/μL solution of Biotinylated Vitronectin | In a 1.5 mL centrifuge tube, 3 μL of 50 mg/mL Biotinamidohexanoic acid N-hydroxysuccinimide ester (from Sigma-Aldrich) in dimethylformamide (from Sigma-Aldrich) was added to 500 μg of Purified Human Vitronectin (from Chemicon International) in buffer (10 mM Sodium Phosphate, pH 7.7, 8 M urea, 5 mM EDTA, 500 mM NaCl). The solution was allowed to incubate at room temperature for one hour and was quenched with 55 μL of 1 M $NH_4OH$. After 5 minutes, the solution was injected into a dialysis cassette, 10,000 MWCO (from Pierce Biotechnology), and was dialyzed against 1× phosphate buffered saline pH 7.4 for 1 hour at 25° C. then overnight at 4° C. 0.7mL was recovered from the cassette, and 40 aliquots of 17.5 μL were prepared providing 0.714 μg/μL each and stored at −80° C. |
| 3.2 0.1 μg/uL solution of NeutrAvidin-HRP | 2 mg of NeutrAvidin Horseradish Peroxidase Conjugated (from Pierce Biotechnology) was dissolved in 1 mL 1× phosphate buffered saline pH 7.4. Of this solution, 75 μL was further diluted 1:20 to 1.5 mL of 0.1 μg/μL with 1× phosphate buffered saline, pH 7.4. 100 aliquots of 15 μL each were prepared and stored at −20° C. |

Test Results

[Structure of "This invention" compound]

[Structure of "Hood et al." compound]

| Test Compound | n = | $R^3$ and $R^4$ | $R^6$ | $IC_{50}$ (nM) | $IC_{50}$ Ratio Relative to Hood et al. |
|---|---|---|---|---|---|
| This invention: | | | | | |
| 1 | 1 | $CH_3$ | Boc | 0.72 ± 0.08 | 17.3 ± 4.7 |
| 3 | 0 | H | Boc | 1.70 ± 0.20 | 8.8 ± 3.5 |
| 5 | 1 | H | Boc | 1.02 ± 0.12 | 11.2 ± 2.4 |
| 7 | 2 | H | Boc | 1.34 ± 0.14 | 10.8 ± 2.7 |
| 2 | 1 | $CH_3$ | H | 2.94 ± 0.19 | 7.0 ± 0.7 |
| 4 | 0 | H | H | 3.64 ± 0.30 | 4.3 ± 0.6 |
| 6 | 1 | H | H | 6.68 ± 0.54 | 3.6 ± 0.7 |
| 8 | 2 | H | H | 3.13 ± 0.33 | 1.3 ± 0.5 |
| Hood et al. | — | — | — | 14.1 ± 1.4 | — |

The foregoing descriptions and examples are offered for purposes of illustration. Further modifications and variations that are still within the scope of the invention will be suggested to those skilled in the art. All published materials cited herein, including technical articles, patents and published patent applications, are hereby incorporated herein by reference in their entirety for all purposes capable of being served thereby.

What is claimed is:

1. A compound having the formula

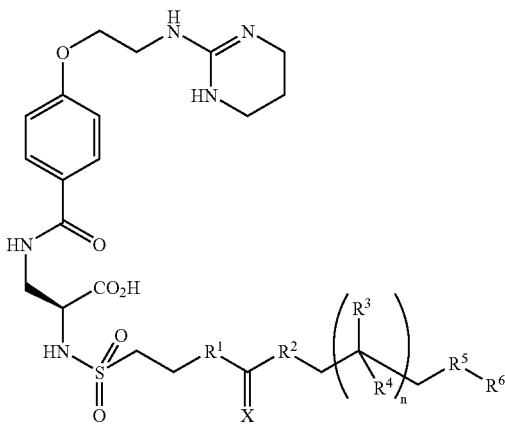

in which:
X is a member selected from the group consisting of NH, O, and S;
n is zero or a positive integer;
$R^1$ is a member selected from the group consisting of $CH_2$, NH, O, and S;
$R^2$ is a member selected from the group consisting of $CHR^7$, $NR^7$, O, and S, in which $R^7$ is H or alkyl;
$R^3$ and $R^4$ are members independently selected from the group consisting of H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, and (hydroxy-substituted aryl)alkyl;
$R^5$ is a member selected from the group consisting of $CH_2$, NH, O, and S;
$R^6$ is a member selected from the group consisting of H and $C(=Y)$—$R^8$—$R^9$, in which:
Y is a member selected from the group consisting of NH, O, and S;
$R^8$ is a member selected from the group consisting of $CHR^{10}$, $NR^{10}$, O, and S, in which $R^{10}$ is either H or alkyl; and
$R^9$ is a member selected from the group consisting of H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, and (hydroxy-substituted aryl)alkyl.

2. The compound of claim 1 wherein $R^3$, $R^4$ and $R^9$ are members independently selected from the group consisting of H, $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl.

3. The compound of claim 1 wherein $R^3$ and $R^4$ are members independently selected from the group consisting of H and $C_1$-$C_3$ alkyl, and $R^9$ is a member selected from the group consisting of H and $C_1$-$C_6$ alkyl.

4. The compound of claim 1 wherein $R^3$ and $R^4$ are members independently selected from the group consisting of H and $C_1$-$C_3$ alkyl, and $R^6$ is a member selected from the group consisting of H and $C(=O)$—O—$R^9$, in which $R^9$ is $C_1$-$C_6$ alkyl.

5. The compound of claim 1 wherein $R^1$ is a member selected from the group consisting of $CH_2$ and NH, and $R^5$ is a member selected from the group consisting of $CH_2$ and NH.

6. The compound of claim 1 wherein n is 0, 1, 2, 3, or 4.

7. The compound of claim 1 wherein n is 0, 1, or 2.

8. The compound of claim 1 wherein X is O or S, and Y is O or S.

9. The compound of claim 1 wherein X is O or S, $R^1$ is $CH_2$ or NH, and $R^5$ is $CH_2$ or NH.

10. The compound of claim 1 wherein n is 0, 1, or 2, $R^3$ and $R^4$ are independently H or $C_1$-$C_3$ alkyl, and $R^8$ is H or $C_1$-$C_6$ alkyl.

11. The compound of claim 1 wherein $R^6$ is $C(=Y)$—$R^8$—$R^9$.

12. The compound of claim 11 wherein Y is O and $R^8$ is O.

13. The compound of claim 11 wherein Y is O, $R^8$ is O, and $R^9$ is a member selected from the group consisting of H, $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl.

14. The compound of claim 11 wherein Y is O, $R^8$ is O, and $R^9$ is H or $C_1$-$C_6$ alkyl.

15. The compound of claim 11 wherein Y is O, $R^8$ is O, $R^9$ is a member selected from the group consisting of $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl, and n is 0, 1, or 2.

16. The compound of claim 11 wherein Y is O, $R^8$ is O, $R^9$ is $C_1$-$C_6$ alkyl, $R^3$ and $R^4$ are independently H or $C_1$-$C_3$ alkyl, and n is 0, 1, or 2.

17. The compound of claim 1 wherein n is 1, X is O, $R^1$ is NH, $R^2$ is O, $R^3$ is $CH_3$, $R^4$ is $CH_3$, $R^5$ is NH, and $R^6$ is $C(=O)$—O—$C_4H_9$.

18. The compound of claim 1 wherein n is 0, X is O, $R^1$ is NH, $R^2$ is O, $R^5$ is NH, and $R^6$ is $C(=O)$—O—$C_4H_9$.

19. The compound of claim 1 wherein n is 1, X is O, $R^1$ is NH, $R^2$ is O, $R^3$ is H, $R^4$ is H, $R^5$ is NH, and $R^6$ is $C(=O)$—O—$C_4H_9$.

20. The compound of claim 1 wherein n is 2, X is O, $R^1$ is NH, $R^2$ is O, $R^3$ is H, $R^4$ is H, $R^5$ is NH, and $R^6$ is $C(=O)$—O—$C_4H_9$.

21. The compound of claim 1 wherein n is 1, X is O, $R^1$ is NH, $R^2$ is O, $R^3$ is $CH_3$, $R^4$ is $CH_3$, $R^5$ is NH, and $R^6$ is H.

22. The compound of claim 1 wherein n is 0, X is O, $R^1$ is NH, $R^2$ is O, $R^5$ is NH, and $R^6$ is H.

23. The compound of claim 1 wherein n is 1, X is O, $R^1$ is NH, $R^2$ is O, $R^3$ is H, $R^4$ is H, $R^5$ is NH, and $R^6$ is H.

24. The compound of claim 1 wherein n is 2, X is O, $R^1$ is NH, $R^2$ is O, $R^3$ is H, $R^4$ is H, $R^5$ is NH, and $R^6$ is H.

25. A pharmaceutical composition comprising a pharmacologically effective amount of a compound having the formula

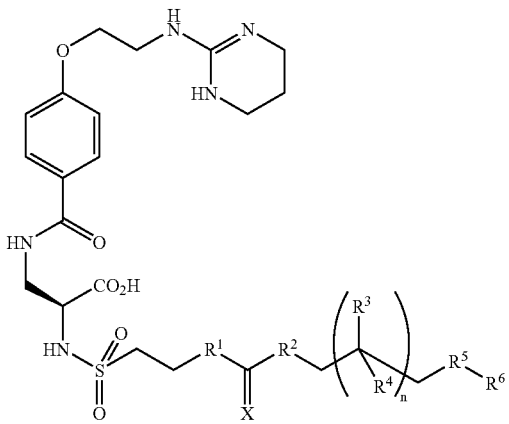

in which:
- X is a member selected from the group consisting of NH, O, and S;
- n is zero or a positive integer;
- $R^1$ is a member selected from the group consisting of $CH_2$, NH, O, and S;
- $R^2$ is a member selected from the group consisting of $CHR^7$, $NR^7$, O, and S, in which $R^7$ is H or alkyl;
- $R^3$ and $R^4$ are members independently selected from the group consisting of H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, and (hydroxy-substituted aryl)alkyl;
- $R^5$ is a member selected from the group consisting of $CH_2$, NH, O, and S;
- $R^6$ is a member selected from the group consisting of H and $C(=Y)-R^8-R^9$, in which:
  - Y is a member selected from the group consisting of NH, O, and S;
  - $R^8$ is a member selected from the group consisting of $CHR^{10}$, $NR^{10}$, O, and S, in which $R^{10}$ is H or alkyl; and
  - $R^9$ is a member selected from the group consisting of H, alkyl, aryl, arylalkyl, cycloalkyl, cycloalkylalkyl, alkyl-substituted aryl, (alkyl-substituted aryl)alkyl, hydroxy-substituted alkyl, hydroxy-substituted aryl, and (hydroxy-substituted aryl)alkyl;

and a pharmaceutically acceptable carrier.

26. The pharmaceutical composition of claim 25 wherein $R^3$, $R^4$ and $R^9$ are members independently selected from the group consisting of H, $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl.

27. The pharmaceutical composition of claim 25 wherein $R^3$ and $R^4$ are members independently selected from the group consisting of H and $C_1$-$C_3$ alkyl, and $R^9$ is a member selected from the group consisting of H and $C_1$-$C_6$ alkyl.

28. The pharmaceutical composition of claim 25 wherein $R^3$ and $R^4$ are members independently selected from the group consisting of H and $C_1$-$C_3$ alkyl, and R is a member selected from the group consisting of H and $C(=O)-O-R^9$, in which $R^9$ is $C_1$-$C_6$ alkyl.

29. The pharmaceutical composition of claim 25 wherein $R^1$ is a member selected from the group consisting of $CH_2$ and NH, and $R^5$ is a member selected from the group consisting of $CH_2$ and NH.

30. The pharmaceutical composition of claim 25 wherein n is 0, 1, 2, 3, or 4.

31. The pharmaceutical composition of claim 25 wherein n is 0, 1, or 2.

32. The pharmaceutical composition of claim 25 wherein X is O or S, and Y is O or S.

33. The pharmaceutical composition of claim 25 wherein X is O or S, $R^1$ is $CH_2$ or NH, and $R^5$ is $CH_2$ or NH.

34. The pharmaceutical composition of claim 25 wherein n is 0, 1, or 2, $R^3$ and $R^4$ are independently H or $C_1$-$C_3$ alkyl, and $R^9$ is H or $C_1$-$C_6$ alkyl.

35. The pharmaceutical composition of claim 25 wherein $R^6$ is $C(=Y)-R^8-R^9$.

36. The pharmaceutical composition of claim 35 wherein Y is O and $R^8$ is O.

37. The pharmaceutical composition of claim 35 wherein Y is O, $R^8$ is O, and $R^9$ is a member selected from the group consisting of H, $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl.

38. The pharmaceutical composition of claim 35 wherein Y is O, $R^8$ is O, and $R^9$ is H or $C_1$-$C_6$ alkyl.

39. The pharmaceutical composition of claim 35 wherein Y is O, $R^8$ is O, $R^9$ is a member selected from the group consisting of $C_1$-$C_6$ alkyl, phenyl, phenyl-substituted $C_1$-$C_6$ alkyl, $C_5$-$C_7$ cycloalkyl, ($C_5$-$C_7$ cycloalkyl)-substituted $C_1$-$C_6$ alkyl, ($C_1$-$C_6$ alkyl)-substituted phenyl, (($C_1$-$C_6$ alkyl)-substituted phenyl)-substituted $C_1$-$C_6$ alkyl, hydroxy-substituted $C_1$-$C_6$ alkyl, hydroxy-substituted phenyl, and (hydroxy-substituted phenyl)-substituted $C_1$-$C_6$ alkyl, and n is 0, 1, or 2.

40. The pharmaceutical composition of claim 35 wherein Y is O, $R^8$ is O, $R^9$ is $C_1$-$C_6$ alkyl, $R^3$ and $R^4$ are independently H or $C_1$-$C_3$ alkyl, and n is 0, 1, or 2.

41. The pharmaceutical composition of claim 25 wherein n is 1, X is O, R is NH, $R^2$ is O, $R^3$ is $CH_3$, $R^4$ is $CH_3$, $R^5$ is NH, and $R^6$ is $C(=O)-O-C_4H_9$.

42. The pharmaceutical composition of claim 25 wherein n is 0, X is O, $R^1$ is NH, $R^2$ is O, $R^5$ is NH, and $R^6$ is $C(=O)-O-C_4H_9$.

43. The pharmaceutical composition of claim 25 wherein n is 1, X is O, $R^1$ is NH, $R^2$ is O, $R^3$ is H, $R^4$ is H, $R^5$ is NH, and $R^6$ is $C(=O)-O-C_4H_9$.

44. The pharmaceutical composition of claim 25 wherein n is 2, X is O, $R^1$ is NH, $R^2$ is O, $R^3$ is H, $R^4$ is H, $R^5$ is NH, and $R^6$ is $C(=O)-O-C_4H_9$.

45. The pharmaceutical composition of claim 25 wherein n is 1, X is O, $R^1$ is NH, $R^2$ is O, $R^3$ is $CH_3$, $R^4$ is $CH_3$, $R^5$ is NH, and $R^6$ is H.

46. The pharmaceutical composition of claim 25 wherein n is 0, X is O, $R^1$ is NH, $R^2$ is O, $R^5$ is NH, and $R^6$ is H.

47. The pharmaceutical composition of claim 25 wherein n is 1, X is O, $R^1$ is NH, $R^2$ is O, $R^3$ is H, $R^4$ is H, $R^5$ is NH, and $R^6$ is H.

48. The pharmaceutical composition of claim 25 wherein n is 2, X is O, R is NH, $R^2$ is O, $R^3$ is H, $R^4$ is H, $R^5$ is NH, and $R^6$ is H.

* * * * *